US012648770B2

(12) United States Patent
Hustedt

(10) Patent No.: US 12,648,770 B2
(45) Date of Patent: Jun. 9, 2026

(54) SUTURE BASED CLAMPING DEVICE

(71) Applicant: Responsive Arthroscopy, Inc.,
Minneapolis, MN (US)

(72) Inventor: Jacob Hustedt, Sandy, UT (US)

(73) Assignee: Responsive Arthroscopy, Inc.,
Minneapolis, MN (US)

( * ) Notice: Subject to any disclaimer, the term of this
patent is extended or adjusted under 35
U.S.C. 154(b) by 370 days.

(21) Appl. No.: 18/305,243

(22) Filed: Apr. 21, 2023

(65) Prior Publication Data

US 2023/0338018 A1      Oct. 26, 2023

Related U.S. Application Data

(60) Provisional application No. 63/363,466, filed on Apr.
22, 2022.

(51) Int. Cl.
*A61B 17/04*            (2006.01)
(52) U.S. Cl.
CPC .. *A61B 17/0401* (2013.01); *A61B 2017/0404*
(2013.01); *A61B 2017/0441* (2013.01); *A61B*
*2017/0459* (2013.01)

(58) Field of Classification Search
CPC ........ A61B 17/0401; A61B 2017/0404; A61B
2017/0441; A61B 2017/0459
See application file for complete search history.

(56) References Cited

U.S. PATENT DOCUMENTS

| | | | | |
|---|---|---|---|---|
| 8,388,655 B2 * | 3/2013 | Fallin | ................. | A61B 17/0487 |
| | | | | 606/103 |
| 2008/0177302 A1 * | 7/2008 | Shurnas | ............. | A61B 17/0401 |
| | | | | 606/228 |
| 2012/0123474 A1 * | 5/2012 | Zajac | ................. | A61B 17/0401 |
| | | | | 606/232 |
| 2012/0123541 A1 * | 5/2012 | Albertorio | ......... | A61B 17/0401 |
| | | | | 606/232 |
| 2013/0172944 A1 * | 7/2013 | Fritzinger | .......... | A61B 17/0401 |
| | | | | 606/232 |
| 2016/0287243 A1 * | 10/2016 | Benedict | ............ | A61B 17/0401 |
| 2017/0231752 A1 * | 8/2017 | Rodriguez | ......... | A61B 17/0401 |
| | | | | 623/13.14 |
| 2018/0249998 A1 * | 9/2018 | Chavan | ............. | A61B 17/0401 |

\* cited by examiner

*Primary Examiner* — Jing Rui Ou
(74) *Attorney, Agent, or Firm* — Goodwin Procter LLP

(57) ABSTRACT

Systems, assemblies, and methods are provided herein for
fastening of one bone to another bone using one or more
sutures. The features herein enable such fastening with a
more accurate strength, and which can be more easily
fastened in-situ.

9 Claims, 33 Drawing Sheets

180

181

180

181

160

161

163

162

160

161

163

162

SUTURE BASED CLAMPING DEVICE

CROSS-REFERENCE

The present application for patent claims the benefit of and priority to U.S. provisional Application No. 63/363,466, filed Apr. 22, 2022, the contents of which is incorporated herein by reference in its entirety

BACKGROUND

Several medical procedures require the fastening of one bone to another bone. Some such procedures include fixation of acromioclavicular separations due to coracoclavicular ligament disruptions, fixation of dorsal distal radioulnar ligament disruptions, stabilization of the first and second metatarsals for hallux valgus reconstruction, and stabilization of the first and second metacarpal when the trapezium has been excised due to osteoarthritis.

SUMMARY

One aspect provided herein is a suture-button system comprising: a) a plurality of suture strands; b) a primary button having a plurality of primary apertures, wherein: a first suture strand of the plurality of suture strands is inserted through a first set of the plurality of primary apertures; and a second suture strand of the plurality of suture strands is inserted through a second set of primary apertures of the plurality of primary apertures; the plurality of primary apertures comprises at least eight primary apertures; the first set is different from the second set; the first set of primary apertures are equally spaced relative to each other in a least a partially circular array, and one or both of the first suture strand and the second suture strand is inserted through the respective first set and second set in a weaving configuration; and c) a secondary button having a plurality of secondary apertures, wherein: the first suture strand and the second suture strand are each inserted through a first and second secondary aperture of the plurality of secondary apertures, such that at least one targeted tissue of a subject is clamped between a distal surface of the primary button and a proximal surface of the secondary button upon applying a tension to one or both of the first suture strand and the second suture strand.

In some embodiments, the first set of primary aperture and the second set of primary apertures are disposed symmetrical to each other on the primary button. In some embodiments, the primary button comprises a primary threaded portion for receiving a secondary threaded portion of a lock, so as to removably couple the lock to the primary button, such that one or both of the first suture strand and the second suture strand are prevented from translating through the respective primary apertures and thereby securing the clamping of the targeted tissue. In some embodiments, the primary threaded portion comprises a female threaded portion. In some embodiments, the lock comprises a head and wherein the secondary threaded portion extends from the head. In some embodiments, a distal surface of the head is tapered outwards from a center axis of the lock. In some embodiments, the lock comprises a driver feature, an alignment feature, or both. In some embodiments, the driver feature and the alignment feature are generally concentric. In some embodiments, a distal surface of the secondary button comprises a channel connecting two or more of the plurality of secondary apertures.

In some embodiments, the suture strand is a #1 size suture, a #2 size suture, a #3 size suture, a #4 size suture, a #5 size suture, a #6 size suture, or a #7 size suture. In some embodiments, the suture strand has a length of about 100 mm to about 1,200 mm. In some embodiments, the system comprises 3, 4, 5, 6 or more suture strands.

In some embodiments, at least one end of the suture strand is coupled to a terminator. In some embodiments, the system further comprises a tightening tool comprising: a) a threaded rod; b) a knob coupled to a proximal end of the threaded rod; c) a collar coupled to the threaded rod; d) an spinner between the knob and the collar, wherein the spinner comprises an aperture accepting the threaded rod; and e) a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driver feature of the lock. In some embodiments, the spinner further comprises a terminator channel accepting the terminator. In some embodiments, the spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature. In some embodiments, the spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod enables for the suture to be tightened, so as to reduce or minimize an amount of slack left in the suture, and/or reduce or minimize future stretching by the suture, thereby keeping the suture clamp tight. In some embodiments, rotating the knob and the threaded rod in a second direction opposite the first direction translates the spinner distally towards the handle. In some embodiments, rotating the handle in a first direction tightens the lock against the primary button.

Another aspect provided herein is a method of securing one or more sutures, the method comprising: a) providing a suture-button system comprising: a first suture strand and a second suture strand, a primary button having a first set of primary apertures and a second set of primary apertures, wherein the first set is different from the second set, a secondary button having a first secondary aperture and a second secondary aperture; b) inserting the first suture strand and the second suture strand each through the first secondary aperture and the second secondary aperture, b) inserting the first suture strand through the first set of primary apertures, wherein i) a first end of the first suture strand is passed through a first primary aperture and a third primary aperture of the first set of primary apertures, the first and third primary apertures not being adjacent to each other, and ii) a second end of the first suture strand is passed through a second primary aperture and a fourth primary aperture of the first set of primary apertures, the second and fourth primary apertures not being adjacent to each other, such that the first and second ends of the first suture strand are in a weaving configuration with one another about the primary button; and d) inserting the second suture strand through the second set of primary apertures, wherein i) a first end of the second suture strand is passed through a first primary aperture and a third primary aperture of the second set of primary apertures, the first and third primary apertures not being adjacent to each other, and ii) a second end of the second suture strand is passed through a second primary aperture and a fourth primary aperture of the second set of primary apertures, the second and fourth primary apertures not being adjacent to each other, such that the first and second ends of the second suture strand are in a weaving configuration with one another about the primary button.

In some embodiments, (b)-(d) occurs in any sequential order. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises tightening one or both of the first suture strand and the second suture strand with respect to the primary button, the secondary button, or both, such that the bone or tissue is clamped between a distal surface of the primary button and the proximal surface of the secondary button upon applying a tension to one or both of the first suture strand and the second suture strand.

In some embodiments, an aspect ratio between a length and width of the secondary button is about 1:1 to about 4:1. In some embodiments, the first set of primary aperture and the second set of primary apertures are disposed symmetrical to each other on the primary button. In some embodiments, the primary button comprises a primary threaded portion for receiving a secondary threaded portion of a lock, so as to removably couple the lock to the primary button, such that one or both of the first suture strand and the second suture strand are prevented from translating through the respective primary apertures and thereby securing the clamping of the targeted tissue. In some embodiments, the method further comprises coupling the secondary threaded portion of the lock with the primary threaded portion of the primary button. In some embodiments, the lock comprises a head and wherein the secondary threaded portion extends from the head. In some embodiments, a distal surface of the head is tapered outwards from a center axis of the lock.

Another aspect provided herein is a suture-button system comprising a) a plurality of suture strands; b) a primary button having a plurality of primary apertures and a primary threaded portion, wherein: i) a first suture strand of the plurality of suture strands is inserted through a first set of the plurality of primary apertures; and ii) a second suture strand of the plurality of suture strands is inserted through a second set of primary apertures of the plurality of primary apertures; and iii) the first set is different from the second set; and c) a secondary button having a plurality of secondary apertures, wherein the first suture strand and the second suture strand are each inserted through a first and second secondary aperture of the plurality of secondary apertures, such that at least one targeted tissue of a subject is clamped between a distal surface of the primary button and a proximal surface of the secondary button upon applying a tension to one or both of the first suture strand and the second suture strand.

In some embodiments, the plurality of primary apertures comprises at least 4 primary apertures. In some embodiments, the plurality of primary apertures are equally spaced on the primary button. In some embodiments, the first set of primary apertures are equally spaced relative to each other and in at least a partially circular array about the primary threaded portion, and the second set of primary apertures are equally spaced relative to each other and in at least a partially circular array about the primary threaded portion.

In some embodiments, a proximal surface of the primary button comprises a countersink. In some embodiments, the primary threaded portion comprises a female threaded portion. In some embodiments, a distal surface of the secondary button comprises a channel connecting two or more of the plurality of secondary apertures. In some embodiments, an aspect ratio between a length and width of the secondary button is about 1:1 to about 4:1.

In some embodiments, the system further comprises a lock having a secondary threaded portion, wherein the secondary threaded portion is configured to be removably coupled to the primary threaded portion, wherein coupling the secondary threaded portion of the lock to the primary threaded portion prevents one or both of the first suture strand and the second suture strand from translating through the plurality of primary apertures, thereby securing the clamping of the targeted tissue. In some embodiments, the lock comprises a head and wherein the secondary threaded portion extends from the head. In some embodiments, a distal surface of the head is tapered outwards from a center axis of the lock. In some embodiments, the distal surface of the head is tapered outwards from a center axis of the lock by about 20° to about 89°. In some embodiments, the lock comprises a driver feature, an alignment feature, or both. In some embodiments, the driver feature and the alignment feature are generally concentric. In some embodiments, the driver feature is proximal to the alignment feature. In some embodiments, a maximum inner diameter of the driver feature is greater than a maximum inner diameter of the alignment feature. In some embodiments, at least a portion of the lock extends beyond a distal face of the primary button when the primary button is coupled to the lock. In some embodiments, a distal face of the primary button extends beyond a distal face of the lock when the primary button is coupled to the lock.

In some embodiments, the suture strand is a #1 size suture, a #2 size suture, a #3 size suture, a #4 size suture, a #5 size suture, a #6 size suture, or a #7 size suture. In some embodiments, the suture strand has a length of about 100 mm to about 1,200 mm. In some embodiments, the system comprises 3, 4, 5, 6 or more suture strands.

In some embodiments, at least one end of the suture strand is coupled to a terminator. In some embodiments, the system further comprises a tightening tool comprising: a) a threaded rod; b) a knob coupled to a proximal end of the threaded rod; c) a collar coupled to the threaded rod; d) an spinner between the knob and the collar, wherein the spinner comprises an aperture accepting the threaded rod; and e) a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driver feature of the lock. In some embodiments, the spinner further comprises a terminator channel accepting the terminator. In some embodiments, the spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature.

In some embodiments, the spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod in a second direction opposite the first direction translates the spinner distally towards the handle. In some embodiments, rotating the handle in a first direction tightens the lock against the primary button.

Another aspect described herein is a method of securing one or more sutures, the method comprising a) providing a suture-button system comprising: i) a first suture strand and a second suture strand, ii) a primary button having a first set of primary apertures and a second set of primary apertures, wherein the first set is different from the second set, and iii) a secondary button having a first secondary aperture and a second secondary aperture; b) inserting the first suture strand and the second suture strand each through the first secondary aperture and the second secondary aperture, c) inserting the first suture strand through a first primary aperture and a second primary aperture of the first set; and d) inserting the second suture strand through a first primary aperture and a second primary aperture of the second set.

In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises tightening one or both of the first suture strand and the second suture strand with respect to the primary button, the secondary button, or both, such that the bone or tissue is clamped between a distal surface of the primary button and the proximal surface of the secondary button upon applying a tension to one or both of the first suture strand and the second suture strand. In some embodiments, an aspect ratio between a length and width of the secondary button is about 1:1 to about 4:1.

In some embodiments, the suture-button system further comprises: a) the primary button having a primary threaded portion; and b) a lock having a secondary threaded portion, wherein the secondary threaded portion is configured to be removably coupled to the primary threaded portion, wherein coupling the secondary threaded portion of the lock to the threaded portion prevents one or both of the first suture strand and the second suture strand from translating through the first set and the second set. In some embodiments, the method further comprises coupling the secondary threaded portion of the lock with the primary threaded portion of the primary button.

In some embodiments, for any method described herein, steps (b) through (d) occurs in any sequential order. In some embodiments, the first set of primary apertures are equally spaced relative to each other and in at least a partially circular array about a primary threaded portion of the primary button, and the second set of primary apertures are equally spaced relative to each other and in at least a partially circular array about the primary threaded portion.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
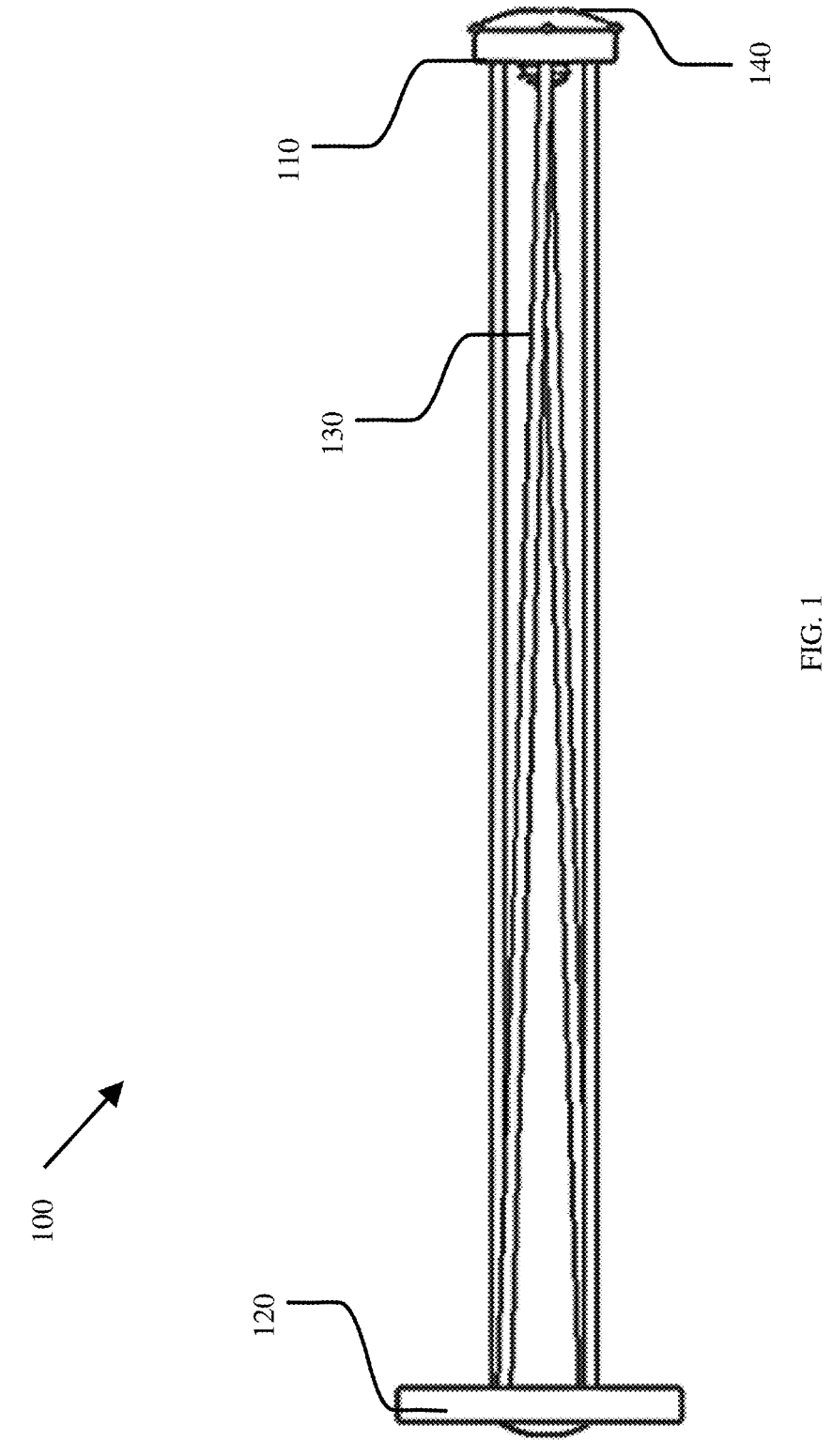
FIG. 1 shows a front-view illustration of an exemplary suture-button assembly, per an embodiment herein.

Potential applications of the devices, systems, and methods herein include but are not limited to fixation of acromioclavicular separations due to coracoclavicular ligament disruptions, fixation of dorsal distal radioulnar ligament disruptions, stabilization of the first and second metatarsals for hallux valgus reconstruction, and stabilization of the first and second metacarpal when the trapezium has been excised due to osteoarthritis.

Suture-Button Systems

One aspect provided herein per FIGS. 1-13B is a suture-button system 100. In some embodiments, the suture-button system comprises one or more suture strands 130, a primary button 110, a secondary button 120, and a lock 140. In some embodiments, the lock 140 couples to the primary button 110. As described herein, for any embodiment, primary button 310 in FIGS. 30A-C may be used instead of or in addition to primary button 110.

In some embodiments, the suture strand 130 is a standard suture. In some embodiments, the suture strand 130 is a medical grade suture. In some embodiments, the suture is a #1 size suture, a #2 size suture, a #3 size suture, a #4 size suture, a #5 size suture, a #6 size suture, or a #7 size suture. In some embodiments, the suture strand 130 has a length of about 100 mm to about 1,200 mm. In some embodiments, the system 100 comprises 2, 3, 4, 5, 6 or more suture strands 130. As disclosed herein, the terms suture and suture strands are used interchangeably.

In some embodiments, per FIGS. 1-4, and 10A-13, the system 100 comprises a first suture strand 130 and a second suture strand 130. In some embodiments, the first suture strand 130 and the second suture strand 130 are bundled 170 together. In some embodiments, per FIGS. 10A and 10B, at least a portion of the second suture strand 130 is hollow or comprises a channel, wherein at least a portion of the first suture strand 130 passes within at least a portion of the hollow portion or the channel of the second suture strand 130 to form a suture bundle 170. In some embodiments, the portion of the first suture strand 130 that passes within the second suture strand 130 is a mesial portion of the first suture. In some embodiments, the portion of the second suture strand 130 through which the first suture strand 130 passes is a mesial portion of the second suture. Alternatively, in some embodiments, the system 100 comprises three or more suture strands 130, wherein one or more of the three or more suture strands 130 are bundled 170 together. In some embodiments, bundling the suture strands 130 together reduces fraying upon contact and/or movement with respect to the secondary button 120. In some embodiments, one or two of the three or more suture strands 130 pass within one or two other passes within at least a portion of another suture strand 130.

In some embodiments, per FIGS. 11A-13, two ends of a suture strand 130 are coupled to each other. Further, in some embodiments two ends of a suture strand 130 are coupled to each other to form a suture loop 132. In some embodiments, two ends of a suture strand 130 are tied together in a knot to form a suture loop. In some embodiments, per FIG. 12, two ends of a suture strand 130 are coupled to each other by a terminator 131. In some embodiments, at least one end of a suture strand 130 is coupled to the terminator 131. In some embodiments, both ends of a suture strand is coupled to a terminator 131. In some embodiments, the terminator is coupled to both ends of the suture to form a suture loop 132. In some embodiments, the terminator 131 is coupled to both ends of each of two sutures to form two suture loops 132. In some embodiments, the terminator 131 is coupled to the suture by a crimp, a fastener, an adhesive, a tie, or any combination thereof. In some embodiments, an outer diameter of the terminator 131 is greater than twice an outer diameter of the suture strands 130. In some embodiments, the suture loops 132 ease hand tensioning.

In some embodiments, tension applied to one or more suture loops adjusts the distance between the primary and secondary buttons. In some embodiments, tension applied to one or more suture loops brings the primary and secondary buttons closer together. In some embodiments, tension applied to one or more suture loops provides a clamping pressure or force about a bone or tissue located between the primary and secondary buttons. In some embodiments, tension is applied by tightening the one or more suture loops. In some embodiments, the one or more suture loops are tightened by pulling on the one or more suture loops. In some embodiments, the one or more suture loops are pulled in a proximal direction relative to the primary button.

Figure 5:
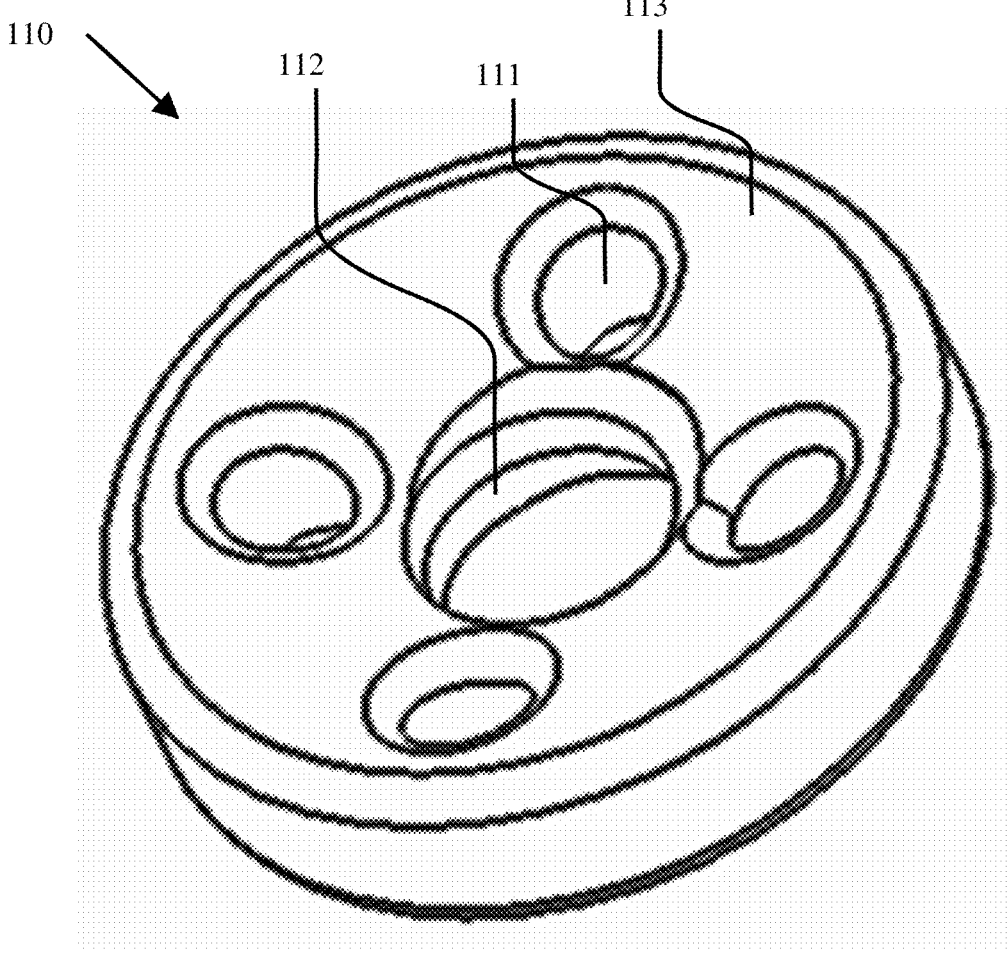
FIG. 5 shows a perspective illustration of an exemplary primary button, per an embodiment herein.

In some embodiments, per FIGS. 5 and 6, the primary button 110 comprises four primary apertures 111 and a primary threaded portion 112. Alternatively, in some embodiments, the primary button 110 comprises 2, 3, 5, 6, 7, 8, 9, 10, 11, 12, or more primary apertures 111. Further, per FIGS. 5 and 6, the four primary apertures 111 are equally spaced apart on the primary button 110 in a circular array about the primary threaded portion 112 and/or about a center axis of the secondary button 120. As shown, the primary apertures 111 are circular. Alternatively, the primary apertures 111 are oblong or polygonal.

Figure 6A:
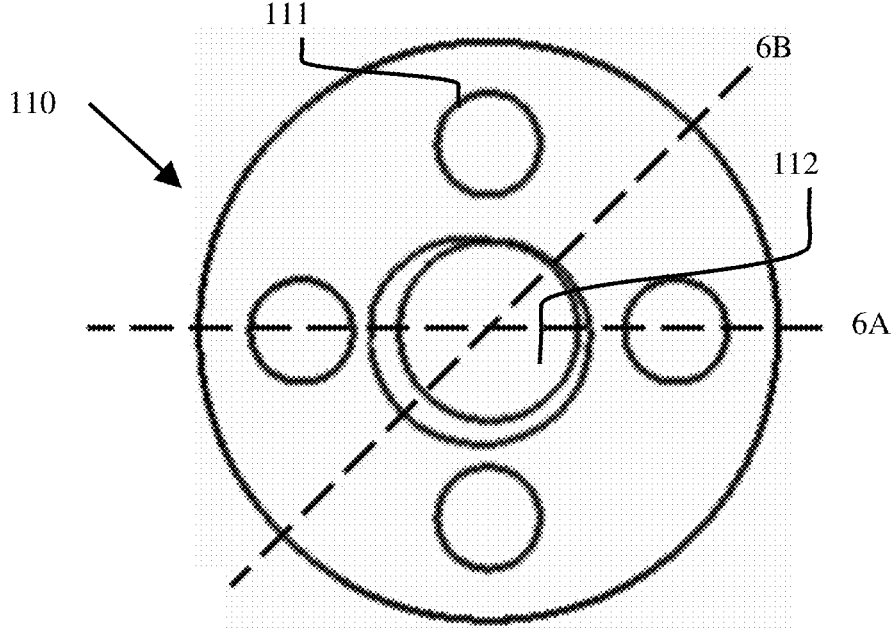
FIG. 6A shows a bottom-view illustration of an exemplary primary button, per an embodiment herein.
Figure 6B:
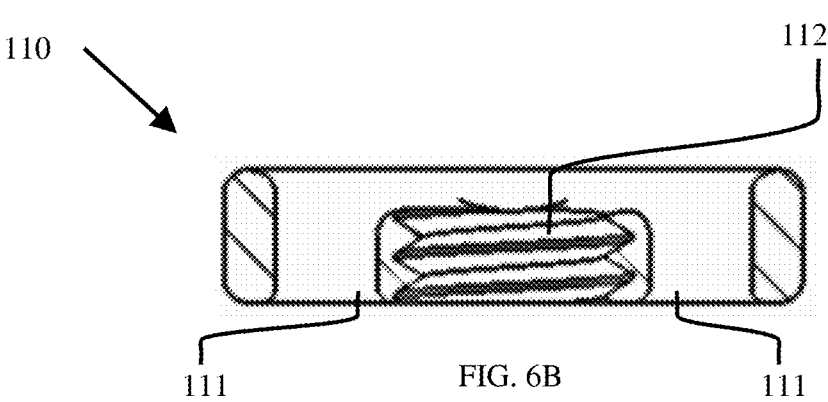
FIG. 6B shows a first cross-sectional illustration of an exemplary primary button, per an embodiment herein.
Figure 6C:
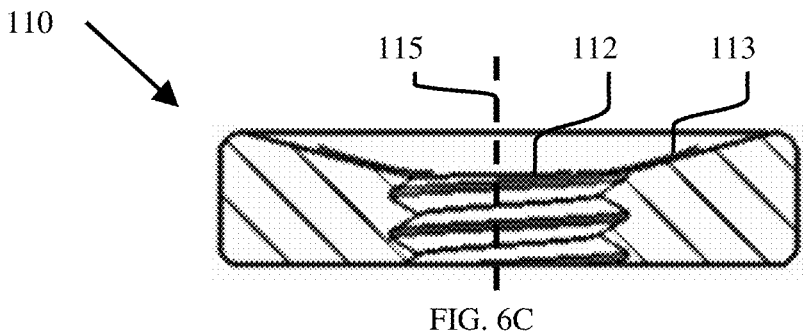
FIG. 6C shows a second cross-sectional illustration of an exemplary primary button, per an embodiment herein.
Figure 8:
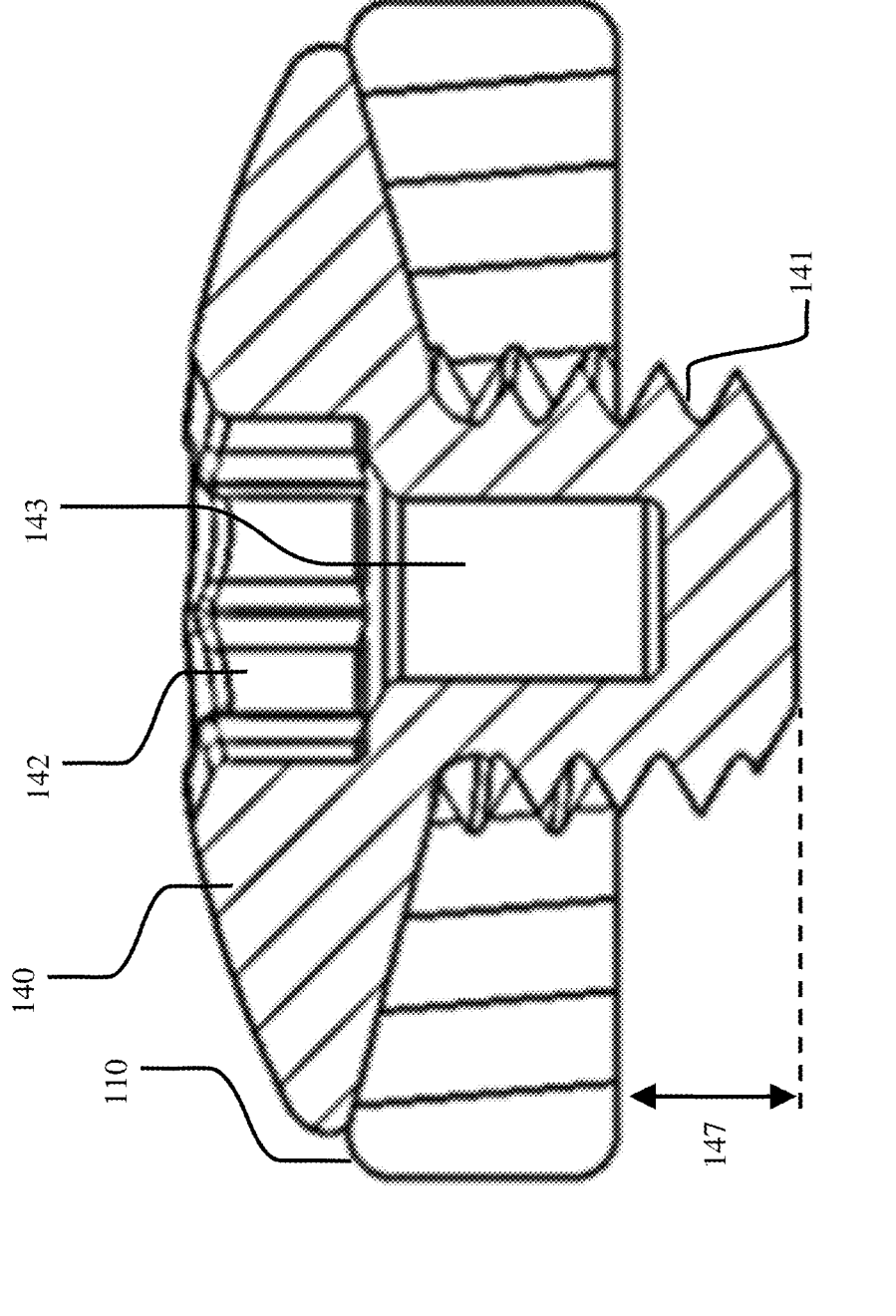
FIG. 8 shows a cross-sectional illustration of an exemplary lock coupled to an exemplary primary button, per an embodiment herein.

In some embodiments, per FIGS. 5, 6C, and 8, a proximal surface 113 of the primary button 110 is tapered towards the primary threaded portion 112. In some embodiments, per FIG. 6C, the proximal surface 113 of the primary button 110 is tapered at an angle of about 30°, about 35°, about 40°, about 45°, about 50°, about 55°, about 60°, about 65°, about 70°, about 75°, about 80°, or about 850 relative to a central axis 115 concentric to the primary threaded portion 112. In some embodiments, the proximal surface 113 of the primary button 110 is tapered at an angle of about 30 to about 85°, including increments therein, relative to a central axis 115 concentric to the primary threaded portion. In some embodiments, the primary button proximal surface 113 is tapered at an angle of about 200 to about 890 relative to the central axis through the primary threaded portion.

As shown in FIGS. 5, 6A-C, and 8, the primary threaded portion 112 comprises a female threaded portion. Further as shown, the primary threaded portion 112 is centered within the proximal surface 113 of the primary button 110. Alternatively, in some embodiments, the primary threaded portion 112 comprises a male threaded portion. In some embodiments, the primary threaded portion 112 comprises a straight threaded portion. In some embodiments, the primary threaded portion 112 comprises a tapered threaded portion. In some embodiments, the primary threaded portion 112 comprises a machine threaded portion. In some embodiments, the primary threaded portion 112 comprises a pipe threaded portion.

In some embodiments, one or more outer edges of the primary button 110 are rounded or chamfered. In some embodiments, one or more edges of the apertures 111 on a distal face of the primary button 110 are rounded or chamfered. In some embodiments, one or more edges of the primary apertures 111 on a proximal face of the primary button 110 are rounded or chamfered. In some embodiments, one or more edges of the primary button 110 are rounded or chamfered. In some embodiments, the rounded or chamfered edges reduce and/or prevent damage to a portion of suture strand 130 passing thereover.

Figure 30B:
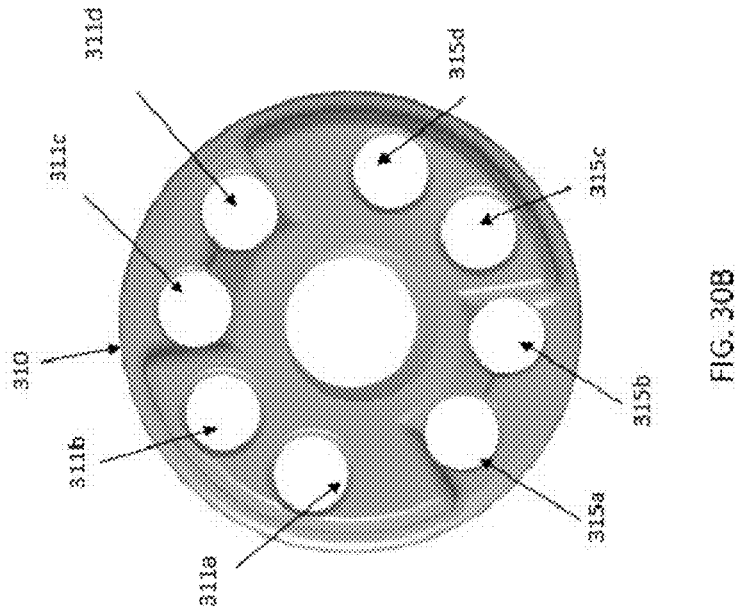
FIG. 30B shows a bottom view of the primary button from FIG. 30A.
Figure 30A:
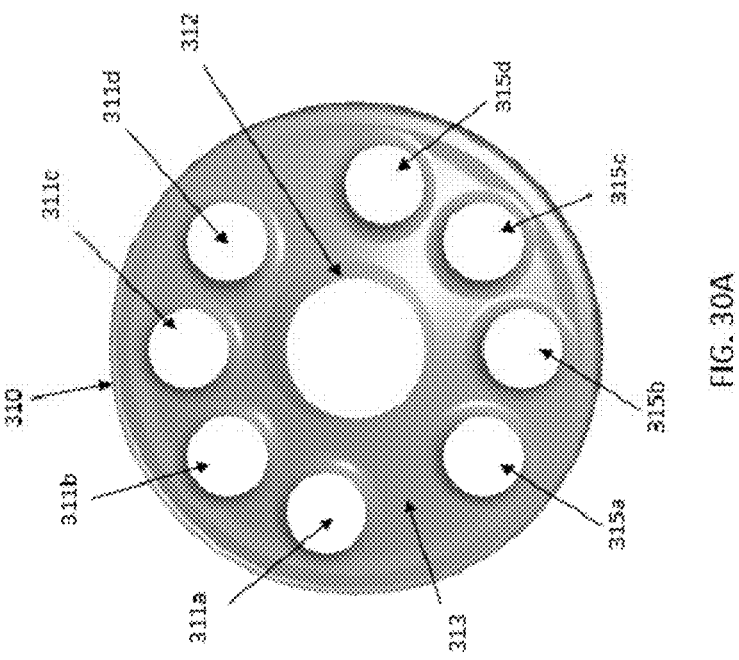
FIG. 30A shows a top view of another exemplary primary button having eight primary apertures, per an embodiment herein.
Figure 30C:
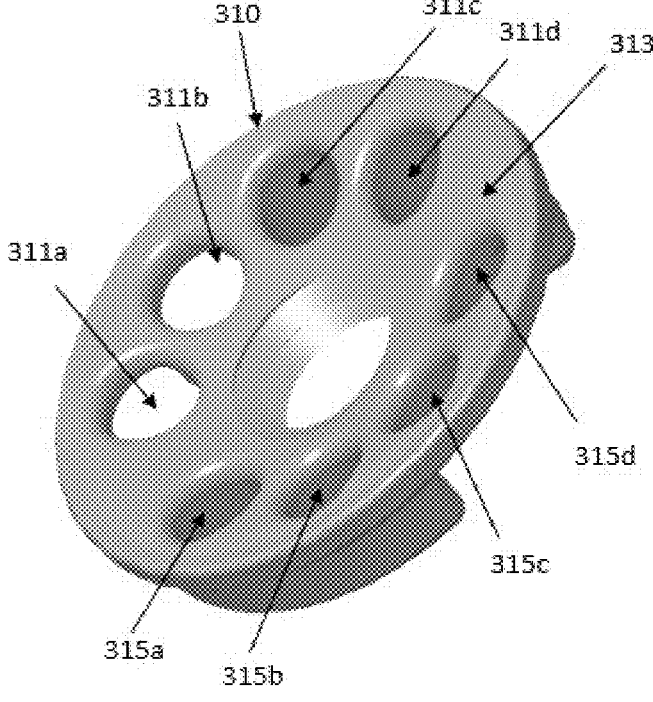
FIG. 30C shows a perspective view of the primary button from FIG. 30A.

In some embodiments, FIGS. 30A-C depict another embodiment of a primary button 310, wherein FIG. 30A depicts a top view of the primary button 310, FIG. 30B depicts a bottom view of the primary button 310, and FIG. 30C, depicts a perspective view of the primary button 310. For any embodiment described herein, the primary button 310 may be used instead of or in addition to primary button 110. In some embodiments, the primary button 310 comprises a plurality of primary apertures, such as eight primary apertures 311, 315 and a primary threaded portion 312. In some embodiments, the plurality of primary apertures are spaced apart according to groups of 2, 3, 4, 5, 6 or more primary apertures. For example, FIGS. 30A-C depict the plurality of primary apertures in groups of 4 (see apertures 311*a-d* and 315*a-d*), wherein the first plurality (e.g., group) of primary apertures 311*a-d* are disposed at a first portion of the primary button 310, and a second plurality of primary apertures 315*a-d* are disposed at a second portion of the primary button 310. In some embodiments, the first plurality of primary apertures 311*a-d* are spaced apart equally between each other, and similarly, the second plurality of primary apertures 315 are spaced apart equally between each other. In some embodiments, the spacing between the first plurality of primary aperture 311 and the second plurality of apertures 315 (e.g., between primary aperture 311*a* and 315*a*, and/or between primary apertures 311*d* and 315*d*) is greater than the spacing of the apertures within each group (e.g., 311, 315), such that the first plurality and second plurality of primary apertures are distinctly separated from each other. In some embodiments, the first plurality and second plurality of apertures 311, 315 are spaced apart on the primary button 310 in a circular array about the primary threaded portion 312 and/or about a center axis of the secondary button 120 (not shown). As shown, the primary apertures 311, 315 are circular. Alternatively, one or more of the primary apertures 311, 315 can be any shape, such as oblong or polygonal.

In some embodiments, per FIG. 30C, a proximal surface 313 of the primary button 310 is tapered towards the primary threaded portion 312. In some embodiments, the proximal surface 313 of the primary button 310 is tapered at an angle of about 30°, about 35°, about 40°, about 45°, about 50°, about 55°, about 60°, about 65°, about 70°, about 75°, about 80°, or about 85° relative to a central axis (e.g., see similar central axis 115 in FIG. 6C). In some embodiments, the proximal surface 313 of the primary button 310 is tapered at an angle of about 20 to about 89°, or about 30 to about 85°, including increments therein, relative to said central axis (e.g., similar to 115) concentric to the primary threaded portion.

In some embodiments, the primary threaded portion 312 comprises a female threaded portion. Further as shown in FIGS. 30A-C, the primary threaded portion 312 is centered within the proximal surface 313 of the primary button 310. Alternatively, in some embodiments, the primary threaded portion 312 comprises a male threaded portion. In some embodiments, the primary threaded portion 312 comprises a straight threaded portion. In some embodiments, the primary threaded portion 312 comprises a tapered threaded portion. In some embodiments, the primary threaded portion 312 comprises a machine threaded portion. In some embodiments, the primary threaded portion 312 comprises a pipe threaded portion.

In some embodiments, one or more outer edges of the primary button 310 are rounded or chamfered. In some embodiments, one or more edges of the apertures 311, 315 on a distal face of the primary button 310 are rounded or chamfered. In some embodiments, one or more edges of the primary apertures 311, 315 on a proximal face of the primary button 310 are rounded or chamfered. In some embodiments, one or more edges of the primary button 310 are rounded or chamfered. In some embodiments, the rounded or chamfered edges reduce and/or prevent damage to a portion of suture strand 330 passing thereover.

Figures 31, 32:
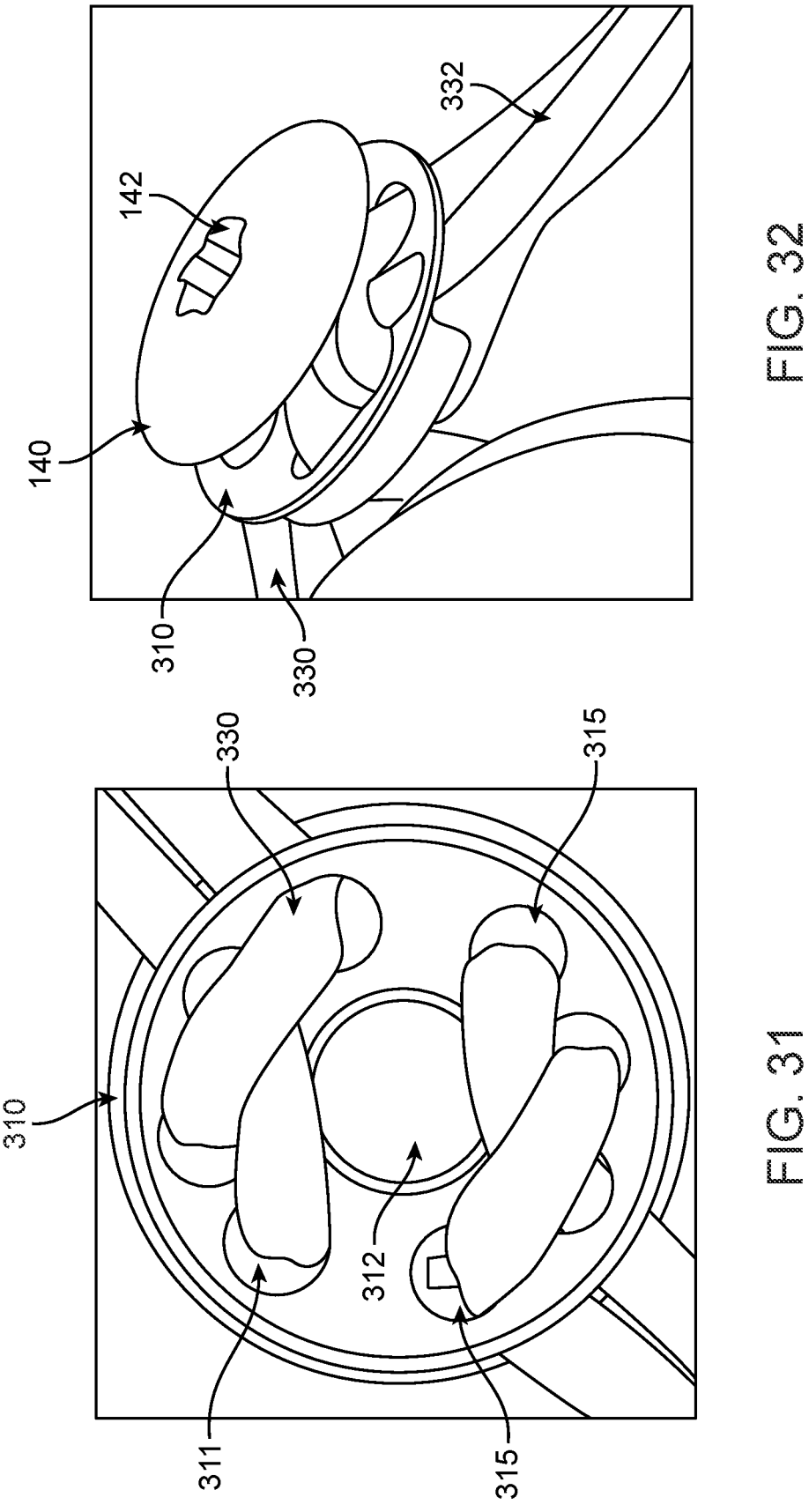
FIG. 31 shows a top view of an image of the primary button from FIG. 30A, further depicting two suture strands passed therethrough.
FIG. 32 shows a perspective view of an image of the primary button and sutures from FIG. 31, further depicting a lock inserted through the primary button.

As described herein, in some embodiments, system 100 comprises primary button 310 instead of or in addition to primary button 110. FIG. 31 depicts an exemplary primary button 310 wherein a first suture strand 330 and a second suture strand 332 is inserted therethrough as part of an embodiment of system 100 described herein. In some embodiments, each suture strand 330, 332 passes through a group of the primary apertures. For example, as depicted in FIG. 31, a first suture strand 330 passes through the first plurality (group) of apertures 311, while a second suture strand 332 passes through the second plurality of apertures 315. In some embodiments, one or both of the first and the second suture strands 330, 332 passes through at least one aperture of both the first and second plurality of apertures 311, 315. In some embodiments, as described herein, each suture strand 330, 332 passes through the primary apertures 311, 315 according to any sequence. For example, as depicted in FIG. 31, the first suture strand 330 passes through at least some of the first plurality of apertures 311 in a weaving configuration, such as one portion of the suture 330 passing through a first primary aperture 311a and a third primary aperture 311c sequentially, and another portion of the suture strand 330 passes through a second primary aperture 311b and a fourth primary aperture 311d sequentially, where the first, second, third, and fourth primary apertures 311a-d are as depicted in FIGS. 30A-D. Similarly, in some embodiments as depicted in FIG. 31, the second suture strand 332 passes through the second plurality of apertures 315 in a weaving configuration. For example, as depicted in FIG. 31, the second suture strand 332 passes through at least some of the second plurality of apertures 315 in a weaving configuration, such as one portion of the suture 332 passing through a fifth primary aperture 315a and a seventh primary aperture 315c sequentially, and another portion of the suture strand 332 passes through a sixth primary aperture 315b and a eighth primary aperture 315d sequentially, where the fifth, sixth, seventh, and eighth primary apertures 315a-d are as depicted in FIGS. 30A-D.

In some embodiments, the first suture strand 330 passes through at least some of the first plurality of apertures 311 and/or at least some of the second plurality of apertures 315 in a non-weaving configuration (such as for example, a first portion of the suture strand 330 passes through a first and second primary aperture 311a-b of the first plurality of apertures 311 sequentially, and a second portion of the suture strand 330 passes through a third and fourth primary aperture 311c-d of the first plurality of sutures sequentially 311). Similarly, in some embodiments, the second suture strand 332 passes through at least some of the first plurality of sutures 311 and/or at least some of the second plurality of sutures 315 in a non-weaving configuration (such as for example, a first portion of the suture 332 passes through a fifth and sixth primary aperture 315a-b of the second plurality of apertures 315 sequentially, and a second portion of the suture passes through a seventh and eight primary aperture 315c-d of the second plurality of apertures 315 sequentially).

Figure 9A:
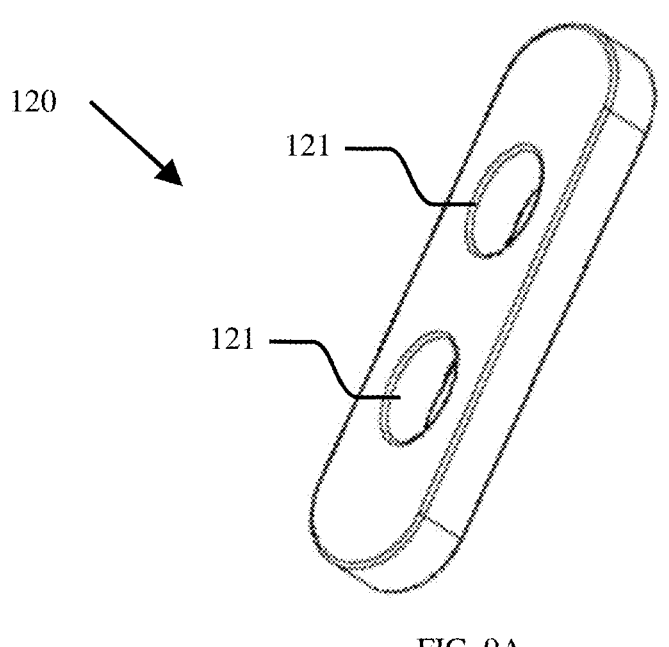
FIG. 9A shows a perspective illustration of an exemplary secondary button, per an embodiment herein.
Figure 9B:
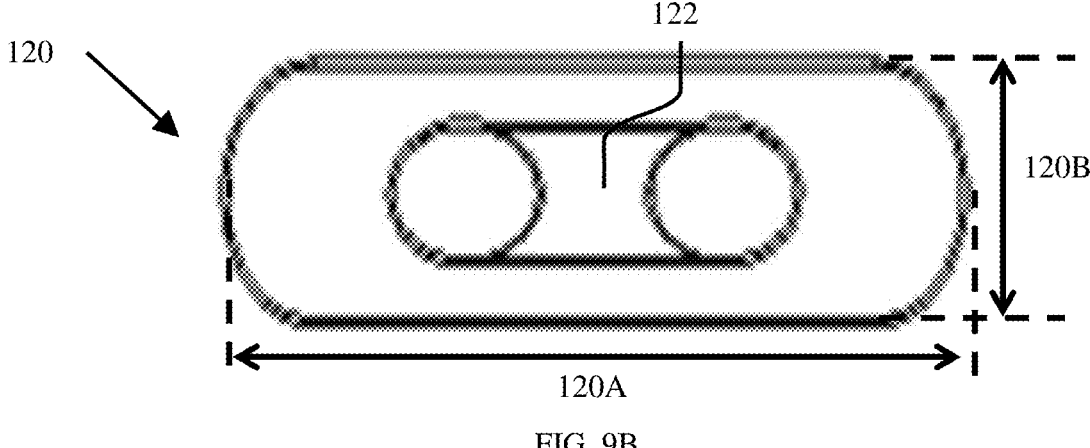
FIG. 9B shows a bottom-view illustration of an exemplary secondary button, per an embodiment herein.
Figure 9C:
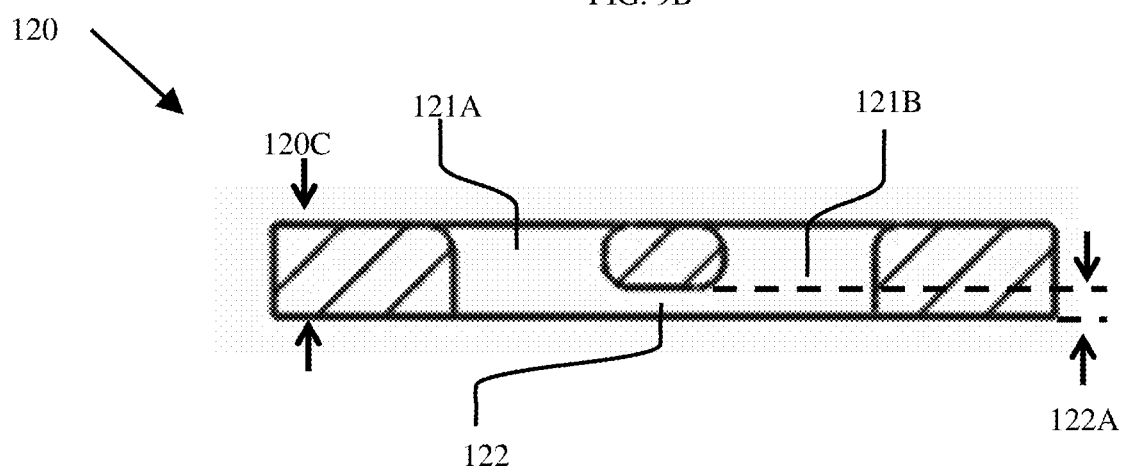
FIG. 9C shows a cross-sectional illustration of an exemplary secondary button, per an embodiment herein.
Figures 10A, 10B:
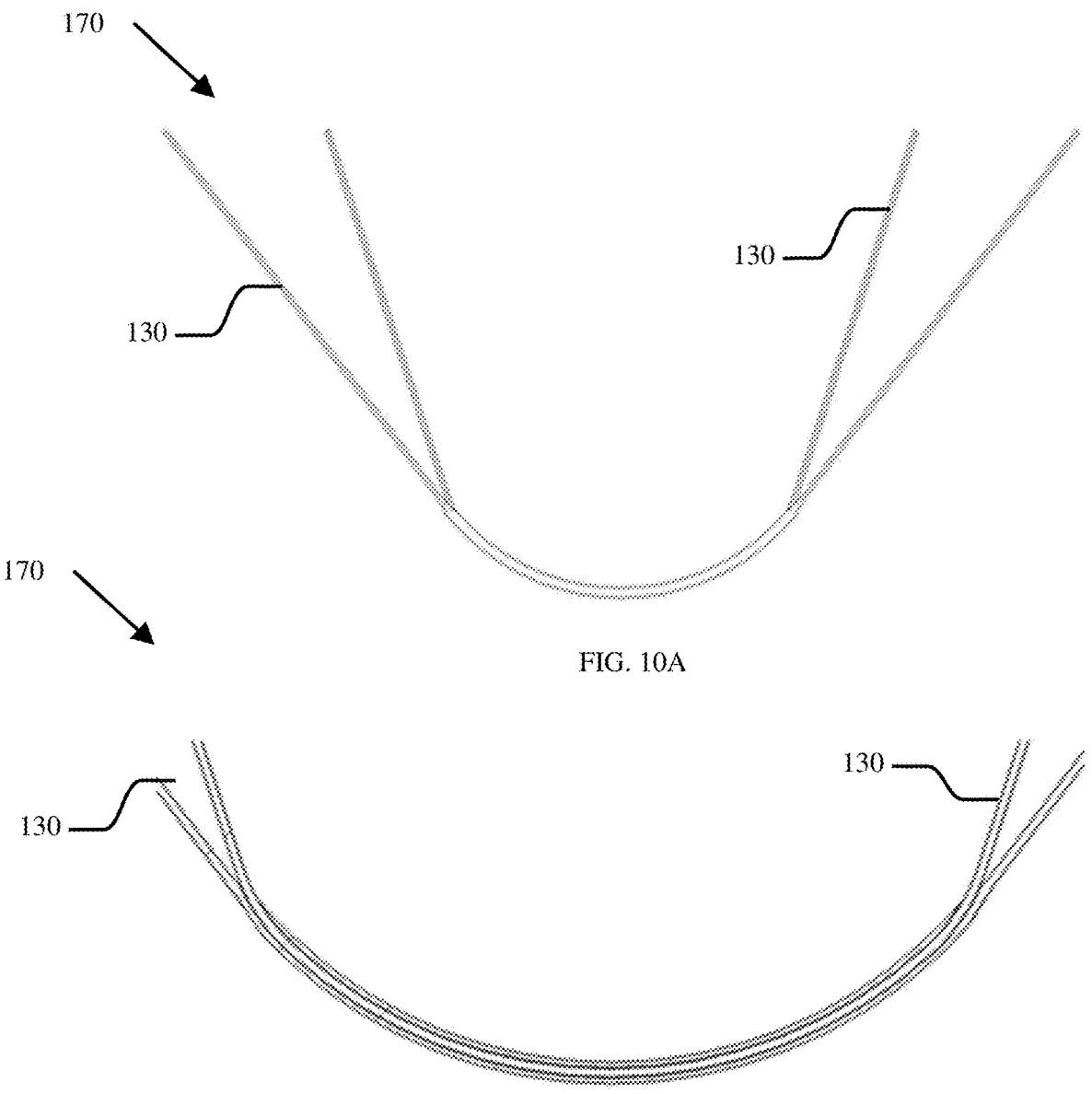
FIG. 10A shows a perspective illustration of an exemplary bundle 170 of sutures, per an embodiment herein.
FIG. 10B shows a cross-sectioned illustration of an exemplary bundle 170 of sutures, per an embodiment herein.

As shown in FIGS. 9A-C, the secondary button 120 comprises a first secondary aperture 121 and a second secondary aperture 121. Alternatively, in some embodiments, the plurality of secondary apertures 121 comprises 3, 4, 5, 6, or more secondary apertures 121. As shown, the secondary apertures 121 are oblong. Alternatively, the secondary apertures 121 are circular or polygonal. In some embodiments, each secondary aperture 121 accepts one or more suture strands 130 therethrough. In some embodiments, each secondary aperture 121 accepts 1, 2, 3, 4, 5, 6 or more suture strands 130 therethrough. In some embodiments, per FIGS. 9B-C, a distal surface of the secondary button 120 comprises a channel 122 connecting two or more of the plurality of secondary apertures 121. As seen the channel 122 has a width equal to an inner width of the first secondary aperture 121, the second secondary aperture 121, or both. In some embodiments, the channel 122 has a depth 122A of about 25% to about 75% of the thickness 120C of the secondary button 120. In some embodiments, an aspect ratio between the length 120A and width 120B of the secondary button 120 is about 1:1 to about 4:1. In some embodiments, the aspect ratio and/or thickness 120C of the secondary button 120 enables its insertion through a narrow cavity in a bone.

In some embodiments, the primary button 110, 310 has a width of about 3 mm to about 12 mm. In some embodiments, the primary button 110, 310 has a length of about 3 mm to about 12 mm. In some embodiments, the primary button 110, 310 has a diameter of about 3 mm to about 12 mm. In some embodiments, the primary button 110, 310 has a thickness of about 0.5 mm to about 3 mm. In some embodiments, the secondary button 120 has a width of about 2 mm to about 7 mm. In some embodiments, the secondary button 120 has a length of about 7 mm to about 20 mm. In some embodiments, the secondary button 120 has a thickness of about 0.5 mm to about 3 mm.

Further per FIG. 9C, in some embodiments, one or more edges of the secondary button 120 are rounded or chamfered. In some embodiments, one or more outer edges of the secondary button 120 are rounded or chamfered. In some embodiments, one or more edges of the secondary apertures 121, the channel 122, or both are rounded or chamfered. In some embodiments, one or more edges of the secondary apertures 121 on a distal face of the secondary button 120 are rounded or chamfered. In some embodiments, one or more edges of the secondary apertures 121 on a proximal face of the secondary button 120 are rounded or chamfered. In some embodiments, the rounded or chamfered edges reduce and/or prevent damage to a portion of suture passing thereover.

In some embodiments, a distance between the centers 121A, 121B of a first secondary aperture 121 and a second secondary aperture 121 is greater than a distance between the centers of at least one pair of opposing primary apertures 111, 311, 315. In some embodiments, a distance between the centers 121A, 121B of the first secondary aperture 121 and the second secondary aperture 121 is less than a distance between the centers of at least one pair of opposing primary apertures 111, 311, 315. In some embodiments, a distance between the centers 121A, 121B of the first secondary aperture 121 and the second secondary aperture 121 is equal to a distance between the centers of at least one pair of opposing primary apertures 111, 311, 315. In some embodiments, a distance between the centers 121A, 121B of the first secondary aperture 121 and the second secondary aperture 121 is greater than a distance between the centers of at least one pair of adjacent primary apertures 111, 311, 315. In some embodiments, a distance between the centers 121A, 121B of the first secondary aperture 121 and the second secondary aperture 121 is less than a distance between the centers of at least one pair of adjacent primary apertures 111, 311, 315. In some embodiments, a distance between the centers 121A, 121B of the first secondary aperture 121 and the second secondary aperture 121 is equal to a distance between the centers of at least one pair of adjacent primary apertures 111, 311, 315.

Per FIGS. 7A-D, the lock 140 comprises a secondary threaded portion 141 and a head 144, wherein the secondary threaded portion 141 extends from the head 144. As shown, the secondary threaded portion 141 comprises a male threaded portion. Alternatively, in some embodiments, the secondary threaded portion 141 comprises a female threaded portion. In some embodiments, the secondary threaded portion 141 comprises a straight threaded portion. In some embodiments, the secondary threaded portion 141 comprises a tapered threaded portion. In some embodiments, the secondary threaded portion 141 comprises a machine threaded portion. In some embodiments, the secondary threaded portion 141 comprises a pipe threaded portion. In some embodiments, the lock 140 comprises a driver feature 142, an alignment feature 143, or both. In some embodiments, the driver feature is disposed at least partially within the head 144. In some embodiments, the driver feature 142 is opposite the secondary threaded portion 141. In some embodiments, the driver feature 142 and the alignment feature 143 are generally concentric. In some embodiments, the driver feature 142 is proximal to the alignment feature 143. In some embodiments, a maximum inner diameter of the driver feature 142 is greater than a maximum inner diameter of the alignment feature 143. In some embodiments, the driver feature comprises a Philips driver feature, a flathead driver feature, a torx driver feature, a hex driver feature, or a square socket feature. In some embodiments, the alignment feature 143 has a cross sectional shape comprising a circle, a triangle, a square, a pentagon, a hexagon, an octagon, or any combination thereof. In some embodiments, a proximal edge of the alignment feature 143 is rounded or chamfered.

Figures 7A, 7B, 7C, 7D:
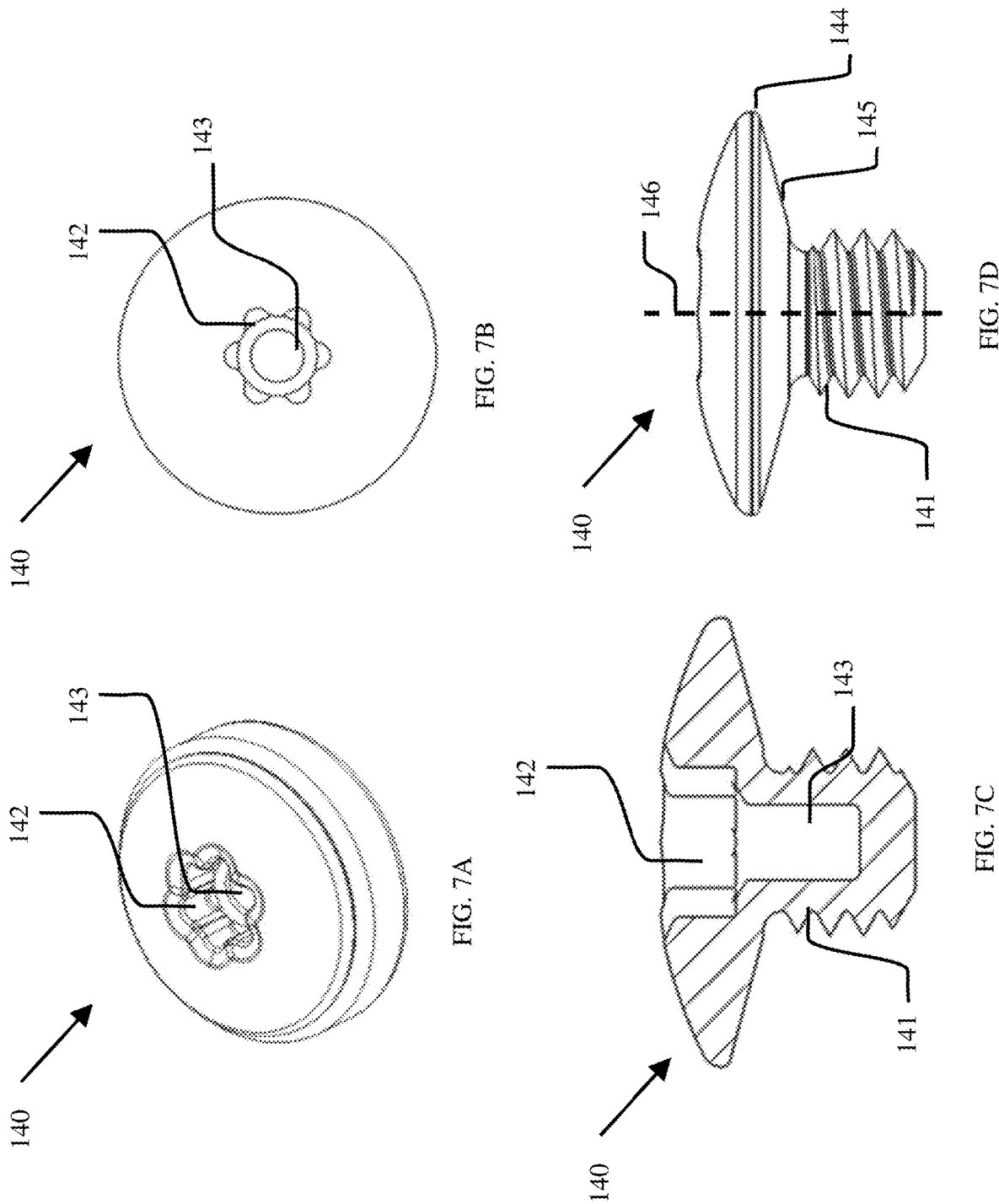
FIG. 7A shows a perspective illustration of an exemplary lock, per an embodiment herein.
FIG. 7B shows a top-view illustration of an exemplary lock, per an embodiment herein.
FIG. 7C shows a cross-sectional illustration of an exemplary lock, per an embodiment herein.
FIG. 7D shows a side view illustration of an exemplary lock, per an embodiment herein.

As shown per FIGS. 7C, 7D, and 8, a distal surface 145 of the head 144 is tapered towards the secondary threaded portion 141. In some embodiments, a distal surface 145 of the head 144 is tapered inward to the center axis 146 of the lock 140. In some embodiments, the distal surface 145 of the head 144 is tapered outwards from the center axis 146 of the lock 140 at an angle of about 20° to about 89° relative to an axis parallel the center axis 146 of the lock 140.

In some embodiments, per FIG. 8, the secondary threaded portion 141 is configured to be removably coupled to the primary threaded portion 112, 312. In some embodiments, coupling the secondary threaded portion 141 of the lock 140 to the primary threaded portion 112, 312 of the primary button 110, 310 prevents the suture strand 130, 330, 332 from translating through one or more of the plurality of first button apertures.

Further per FIG. 8, at least a portion of the tapered distal face 145 of lock 140 seats against the tapered portion of the primary button proximal surface 113, 313 of the primary button 110, 310. In some embodiments, the angle that the distal face of the lock 140 tapers is equivalent to an angle that the primary button proximal face 113, 313 tapers towards the primary threaded portion. In some embodiments, the angle between the proximal surface 113, 313 of the primary button 110, 310 relative to its central axis (see reference character 115 in FIG. 6C for example), and the angle between the distal surface 145 of the head 144 relative to the center axis 146 of the lock 140 are complementary. In some embodiments, the angle between the proximal surface 113, 313 of the primary button 110, 310 relative to its central axis (e.g., 115), and the angle between the distal surface 145 of the head 144 relative to the center axis 146 of the lock 140 are equal. In some embodiments, at least a portion of the distal surface 145 of the head 144, the proximal surface 113, 313 of the primary button 110, 310, or both have a texture configured to increase friction against the suture strand 130, 330, 332.

FIG. 32 depicts an exemplary image of a lock 140 wherein a secondary threaded portion 141 (not shown) is inserted at least partially within a primary threaded portion 312 of a primary button 310, as described herein. As depicted and described herein, the inserted lock 140 secures the positioning and/or tensioning of the sutures 330, 332.

Figures 11A, 11B:
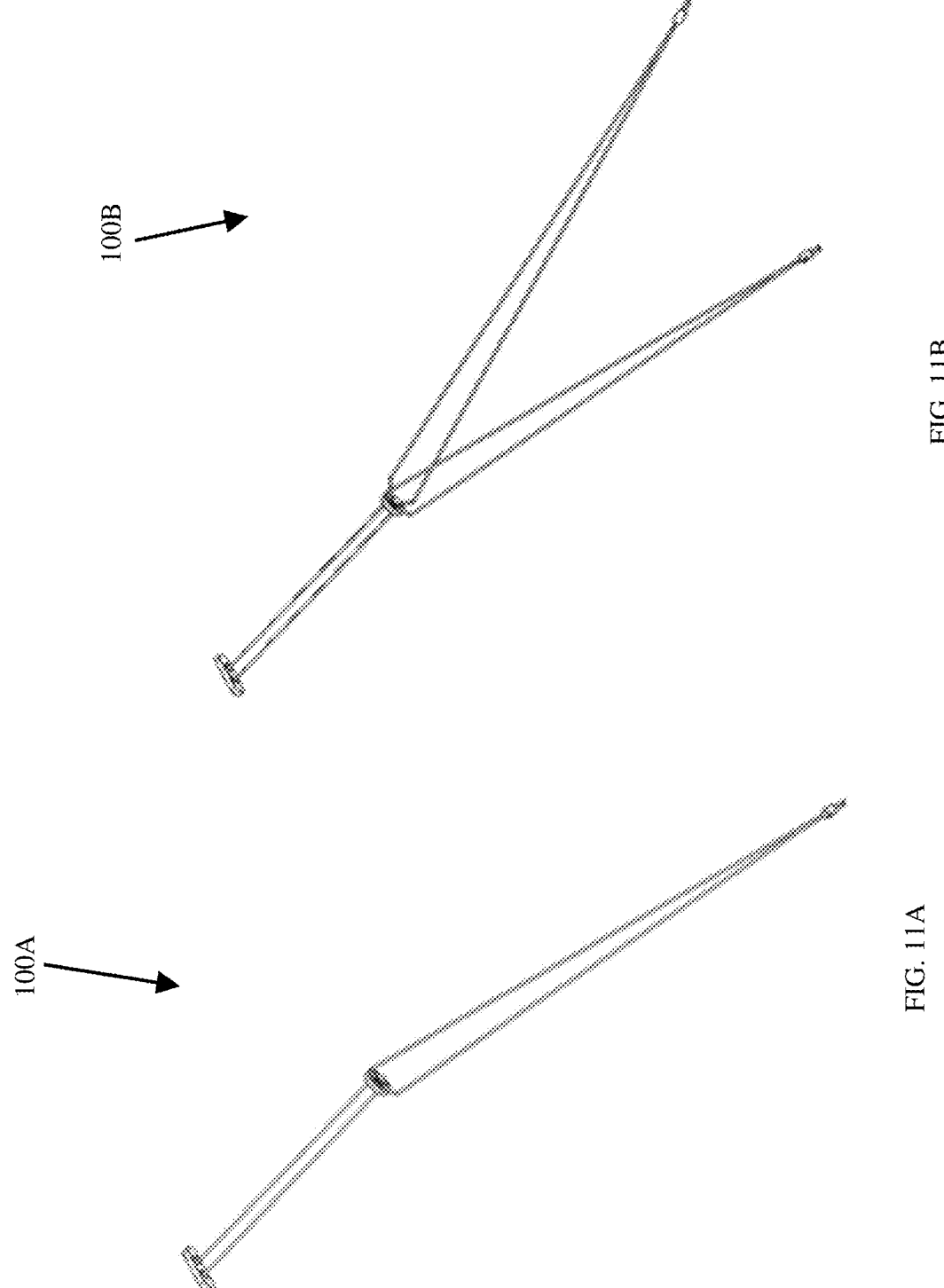
FIG. 11A shows a perspective illustration of an exemplary suture-button assembly with a first suture loop, per an embodiment herein.
FIG. 11B shows a perspective illustration of an exemplary suture-button assembly with a first suture loop and a second suture loop, per an embodiment herein.
Figure 12:
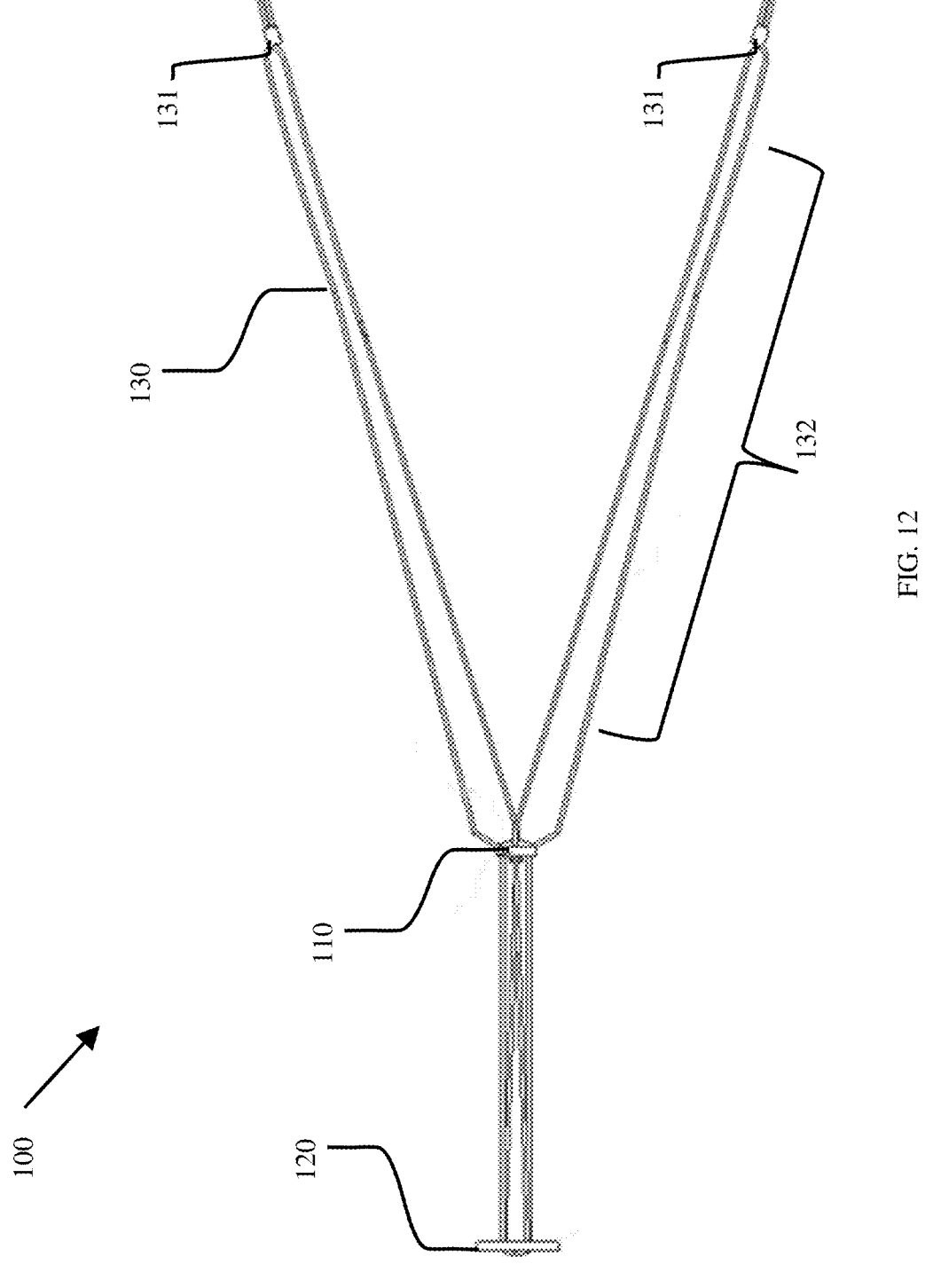
FIG. 12 shows an illustration of an exemplary suture-button assembly with a first suture loop and a second suture loop, per an embodiment herein.

In some embodiments of a first suture-button system 100A, per FIG. 11A, the primary button comprises a first primary aperture and a second primary aperture, the secondary button comprises a first secondary aperture and a second secondary aperture, and a single suture strand passes through the apertures of the primary and secondary buttons. In some embodiments of a second suture-button system 100, per FIGS. 1, 2, 3, 11B and 12, the primary button comprises a first primary aperture, a second primary aperture, a third primary aperture, and a fourth primary aperture, the secondary button comprises a first secondary aperture and a second secondary aperture, and a first suture strand and a second suture strand pass through one or more apertures of the primary and secondary buttons.

Figure 33:
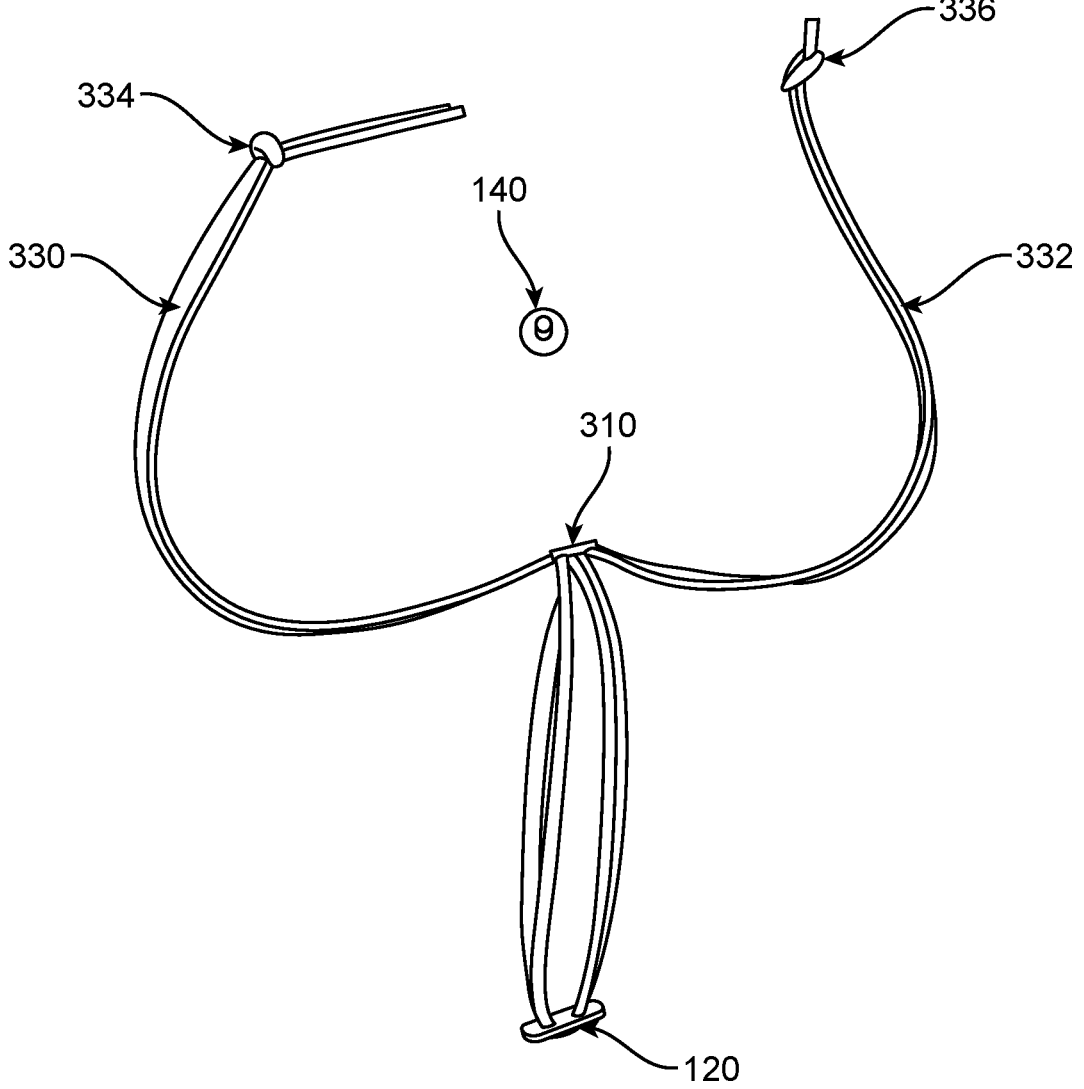
FIG. 33 shows a top view of an image of a suture system, per an embodiment herein, comprising the primary button and sutures from FIG. 31.

In some embodiments of a third suture system 100, FIG. 33 depicts an image of a primary button 310, a secondary button 120, and sutures 330, 332, wherein lock 140 is shown prior to being inserted within the primary threaded portion 312 of the primary button 310. In some embodiments, a first portion of the first suture strand 330 is passed through a secondary aperture (in the secondary button 120), a first primary aperture and a third primary aperture of the first plurality of primary apertures 311, while a second portion of the first suture 330 is passed through the other secondary aperture (in the secondary button 120), a second primary aperture and a fourth primary aperture of the first plurality of primary apertures 311, wherein a suture end for each portion of the suture strand 330 is knotted 334 together. Similarly, in some embodiments, a first portion of the second suture 332 is passed through a secondary aperture (in the secondary button 120), a fifth primary aperture and a seventh primary aperture of the second plurality of primary apertures 315, while a second portion of the second suture strand 332 is passed through the other secondary aperture (in the secondary button 120), a sixth primary aperture and an eighth primary aperture of the second plurality of primary apertures 315, wherein a suture end for each portion of the suture strand 332 is knotted 336 together.

Figure 2:
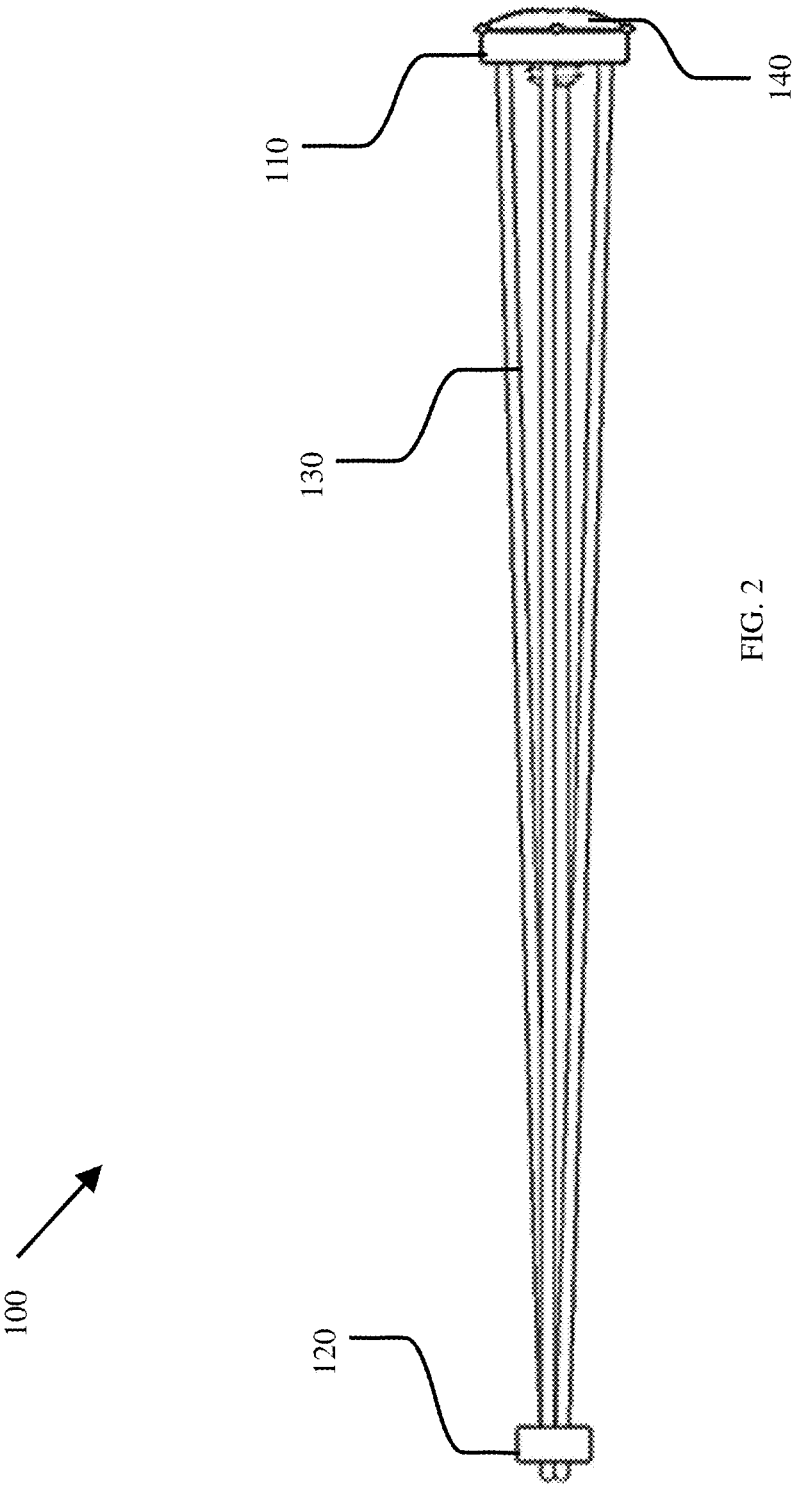
FIG. 2 shows a right-side-view illustration of an exemplary suture-button assembly, per an embodiment herein.
Figure 3:
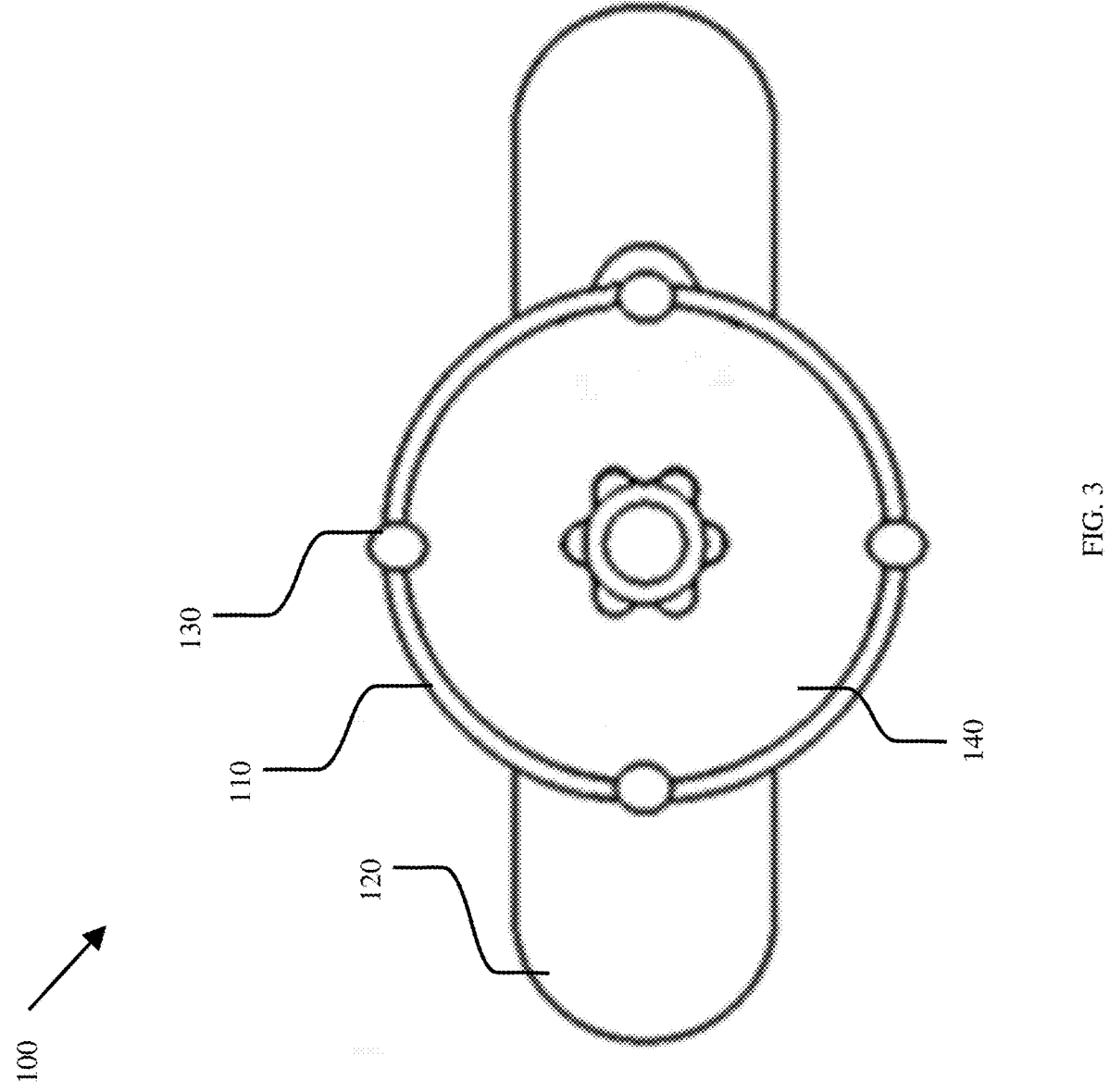
FIG. 3 shows a top-view illustration of an exemplary suture-button assembly, per an embodiment herein.
Figure 4:
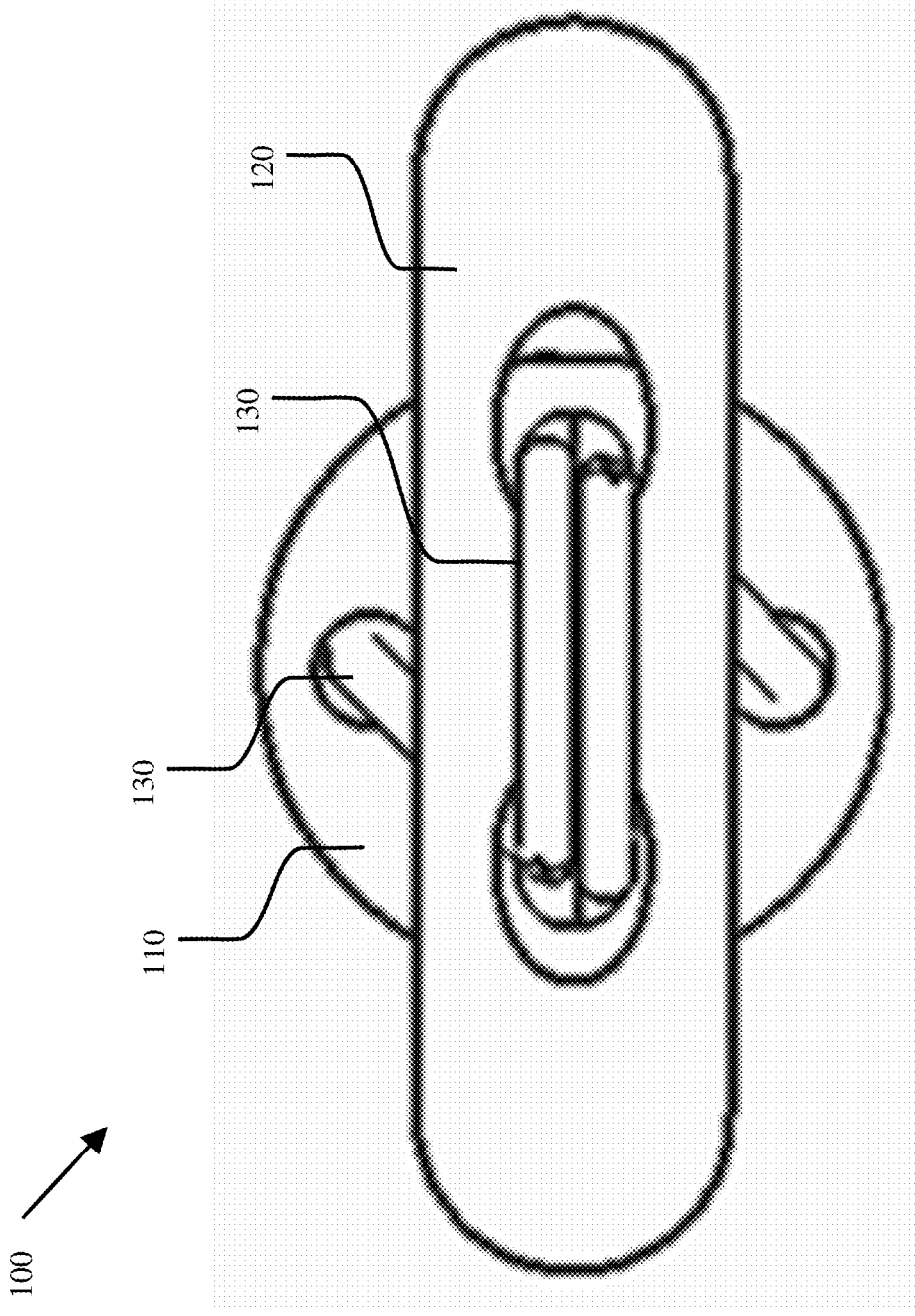
FIG. 4 shows a bottom-view illustration of an exemplary suture-button assembly, per an embodiment herein.

Per FIGS. 1, 2, and 3, for the second suture button assembly, each primary aperture 111 of the primary button has one suture strand 130 inserted therethrough. Alternatively, in some embodiments, each primary aperture 111 has two or more of the plurality of suture strands inserted therethrough. In some embodiments, each primary aperture 111 has 2, 3, 4, 5, 6 or more suture strands inserted therethrough. In some embodiments, each secondary aperture 121 has one or more of the plurality of suture strands inserted therethrough. Per FIGS. 1, 2 and 4, each secondary aperture 121 has two suture strands 130 inserted therethrough. As shown, each secondary aperture 121 has one suture strand 130 inserted distally and one suture strand 130 inserted proximally therethrough. Alternatively, each secondary aperture 121 has two suture strands 130 inserted distally therethrough. Alternatively, each secondary aperture 121 has two suture strands 130 inserted proximally therethrough. Alternatively, in some embodiments, each secondary aperture 121 has three or more sutures strands 130 inserted therethrough. In some embodiments, each secondary aperture 121 has 2, 3, 4, 5, 6 or more sutures strands 130 inserted therethrough.

Per FIG. 3, once the plurality of suture strands has been inserted through the apertures of the primary and secondary buttons, coupling the lock 140 to the primary button 110 prevents each of the plurality of suture strands 130 from translating through one or more of the plurality of primary apertures 111. In some embodiments, coupling the lock 140 to the primary threaded portion 141 prevents each of the plurality of suture strands 130 from translating through one or more of the plurality of primary apertures by compressing at least a portion of each of the plurality of suture strands 130 between the distal face 145 of the lock 140 and the primary button proximal face 113.

In some embodiments, rotating the lock 140 in a first direction relative to the primary button inserts the secondary threaded portion 141 of the lock 140 distally through the primary threaded portion 113 of the primary button 110, so as to compress at least a portion of each of the plurality of suture strands 130 located between the distal face 145 of the head 144 and the primary button proximal face 113. In some embodiments, rotating the lock 140 in a second direction relative to the primary button, opposite the first direction, translates the secondary threaded portion 141 of the lock 140 proximally through the primary threaded portion 113 of the primary button 110, so as to enable each of the plurality of suture strands 130 to translate through the plurality of primary apertures 111.

In some embodiments, per FIG. 8, at least a portion of the lock 140 extends beyond a distal face of the primary button 110 when the primary button 110 is coupled to the lock 140. In some embodiments, a distal face of the primary button 110 extends beyond a distal end of the secondary threaded portion 141 of the lock 140 when the primary button 110 is coupled to the lock 140. In some embodiments, at least a portion of the lock 140 extends beyond a distal face of the primary button 110 by an extension distance 147 of about 1 mm, 2 mm, 3 mm, 4 mm, 5 mm, 6 mm, 7 mm, 8 mm, 9 mm, 10 mm, or more when the primary button 110 is coupled to the lock 140. In some embodiments, a distal face of the primary button 110 extends beyond a distal end of the secondary threaded portion 141 of the lock 140 by an extension distance of about 1 mm, 2 mm, 3 mm, 4 mm, 5 mm, 6 mm, 7 mm, 8 mm, 9 mm, 10 mm, or more when the primary button 110 is coupled to the lock 140. In some embodiments, at least a portion of the lock 140 extends beyond a distal face of the primary button 110 into a bone or tissue. In some embodiments, at least a portion of the lock 140 extends beyond a distal face of the primary button 110 into a bone or tissue tunnel or hole. In some embodiments, at least a portion of the lock 140 extends beyond a distal face of the primary button 110 into a bone or tissue tunnel or hole when the primary button 110 is in contact with the bone or tissue tunnel.

Figure 13:
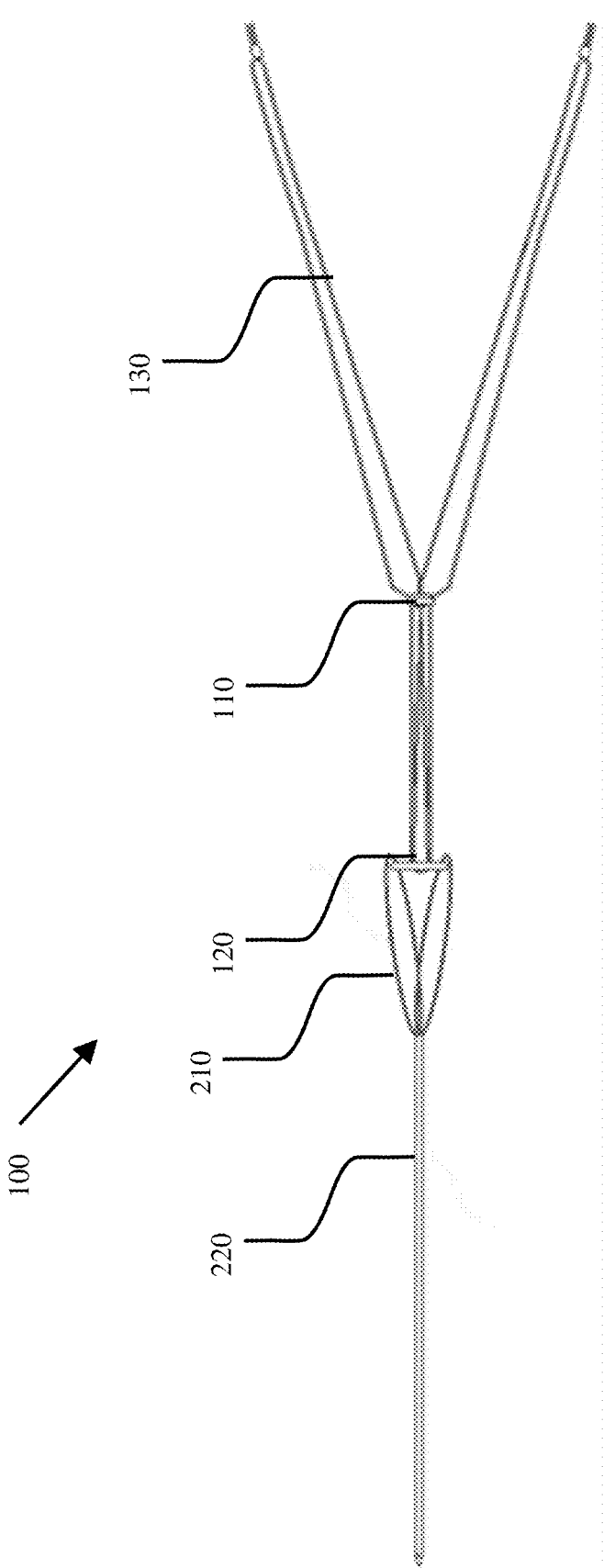
FIG. 13 shows a top-view illustration of an exemplary suture-button assembly with an insertion needle 220 device, per an embodiment herein.
Figures 14A, 14B:
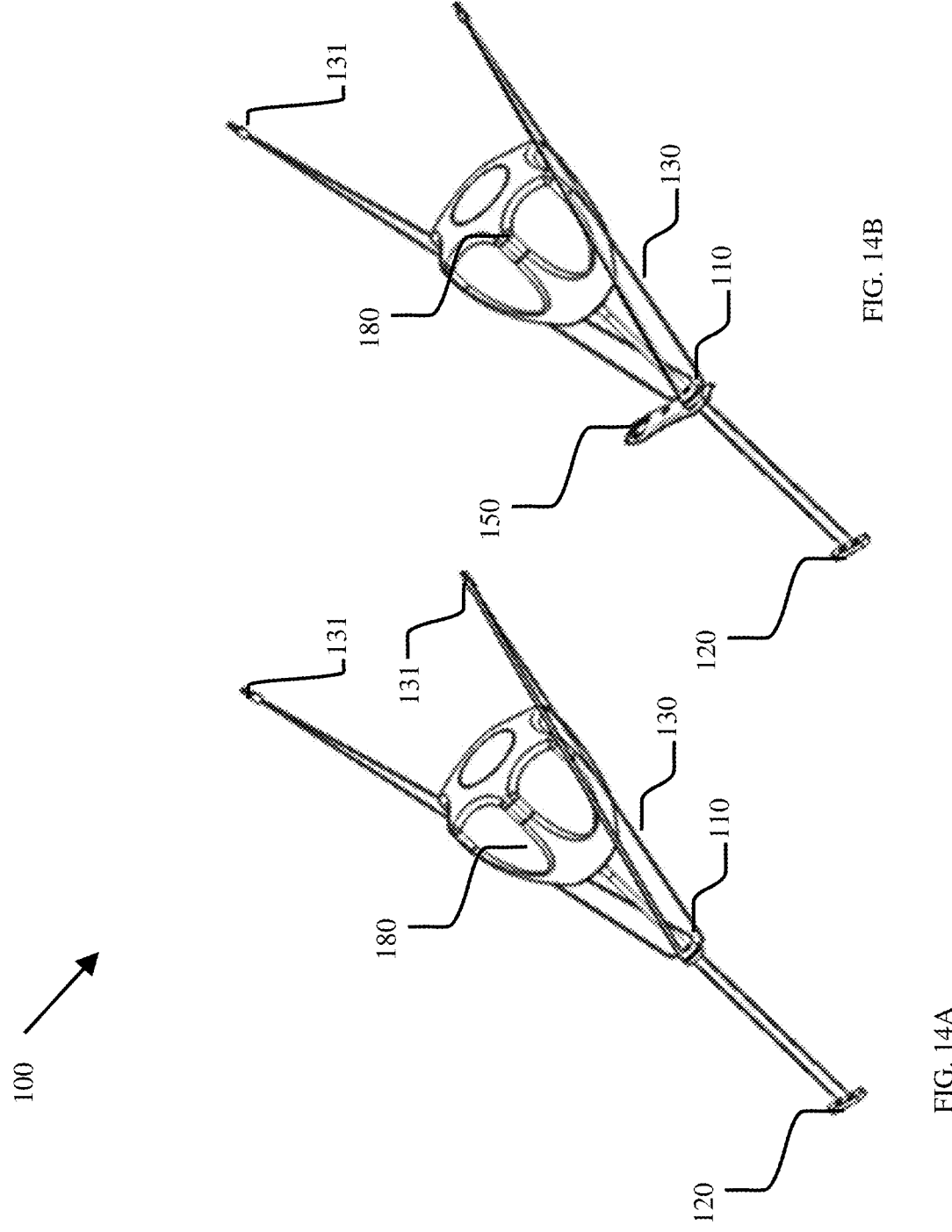
FIG. 14A shows a perspective illustration of an exemplary suture-button assembly with an exemplary lock driver, per an embodiment herein.
FIG. 14B shows a perspective illustration of an exemplary suture-button assembly with an exemplary lock driver and an exemplary insertion plate, per an embodiment herein.
Figures 15A, 15B:
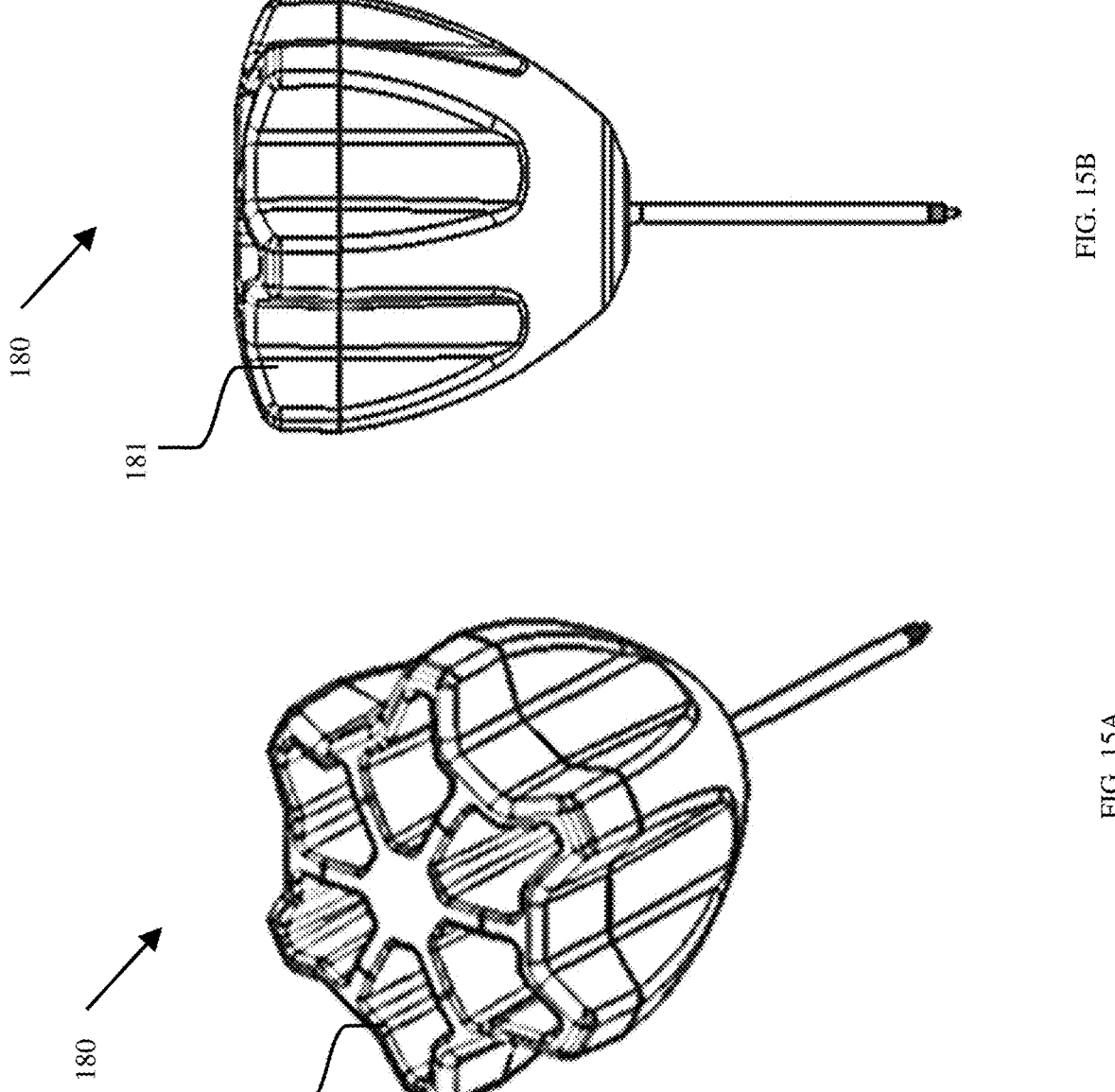
FIG. 15A shows a perspective illustration of an exemplary lock driver, per an embodiment herein.
FIG. 15B shows a front-view illustration of an exemplary lock driver, per an embodiment herein.
Figure 16B:
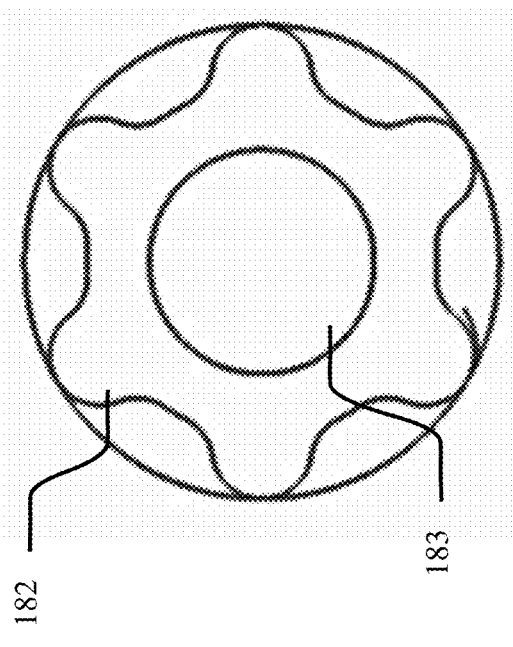
FIG. 16B shows a bottom-view illustration of an exemplary lock driver, per an embodiment.
Figure 16A:
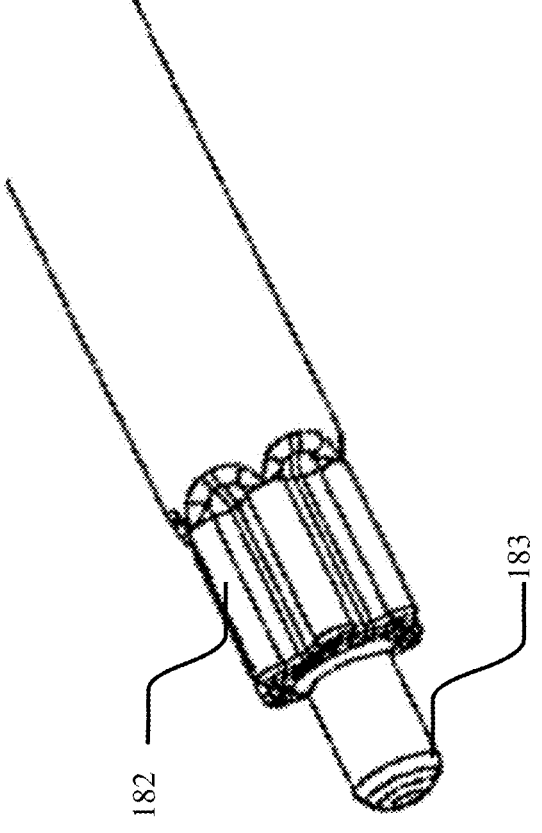
FIG. 16A shows a detailed perspective illustration of an exemplary lock driver, per an embodiment herein.
Figures 17A, 17B, 17C, 17D:
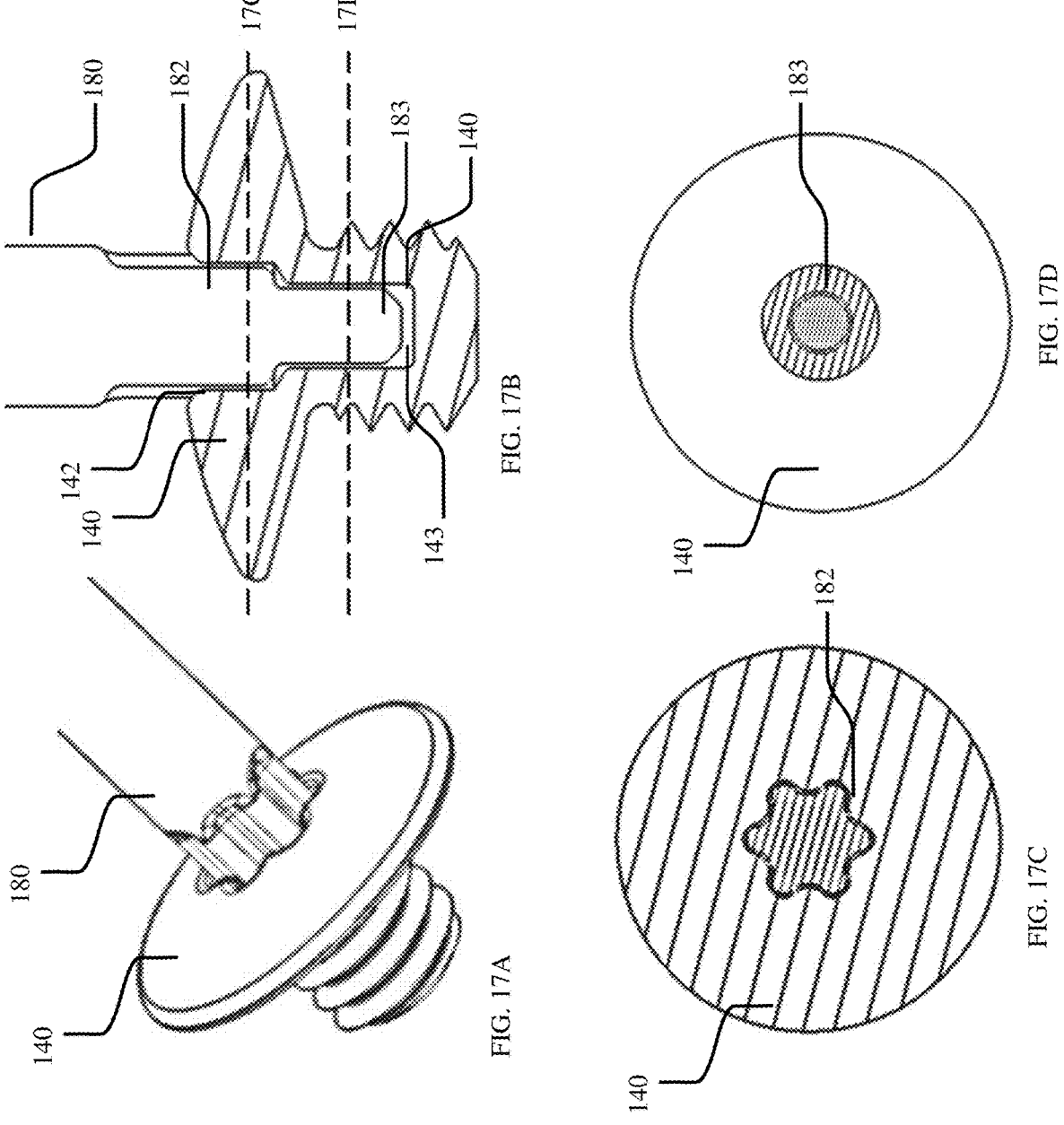
FIG. 17A shows a detailed perspective illustration of the driving feature of an exemplary lock driver rotating the lock, per an embodiment herein.
FIG. 17B shows a front cross-sectioned illustration of the driving feature and the aligning feature of an exemplary lock driver rotating the lock, per an embodiment herein.
FIG. 17C shows a first front cross-sectioned illustration of the driving feature and the aligning feature of an exemplary lock driver rotating the lock, per an embodiment herein.
FIG. 17D shows a second front cross-sectioned illustration of the driving feature and the aligning feature of an exemplary lock driver rotating the lock, per an embodiment herein.
Figure 18:
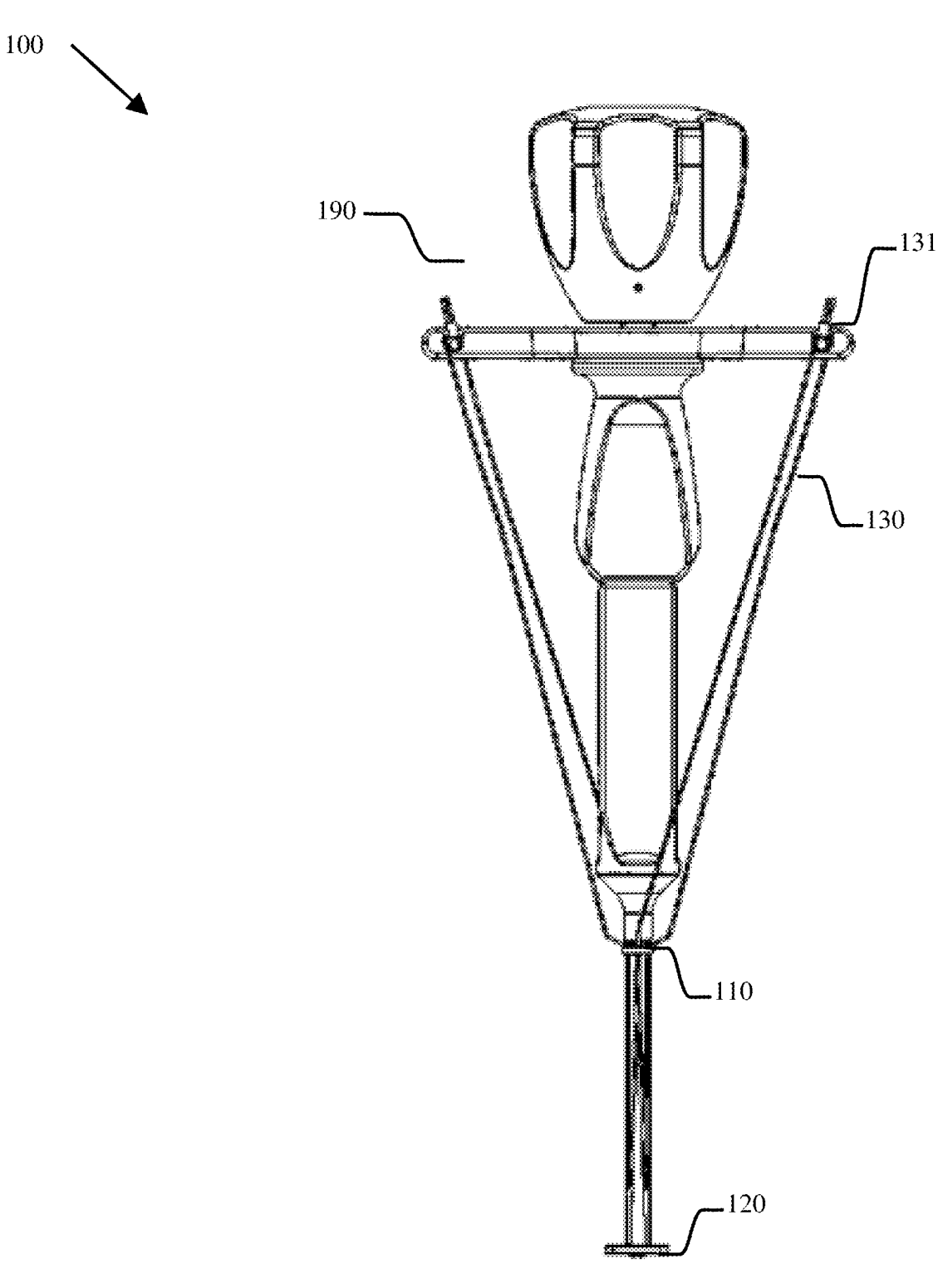
FIG. 18 shows a front-view illustration of an exemplary suture-button system having a tightening tool, per an embodiment.
Figures 19A, 19B, 19C:
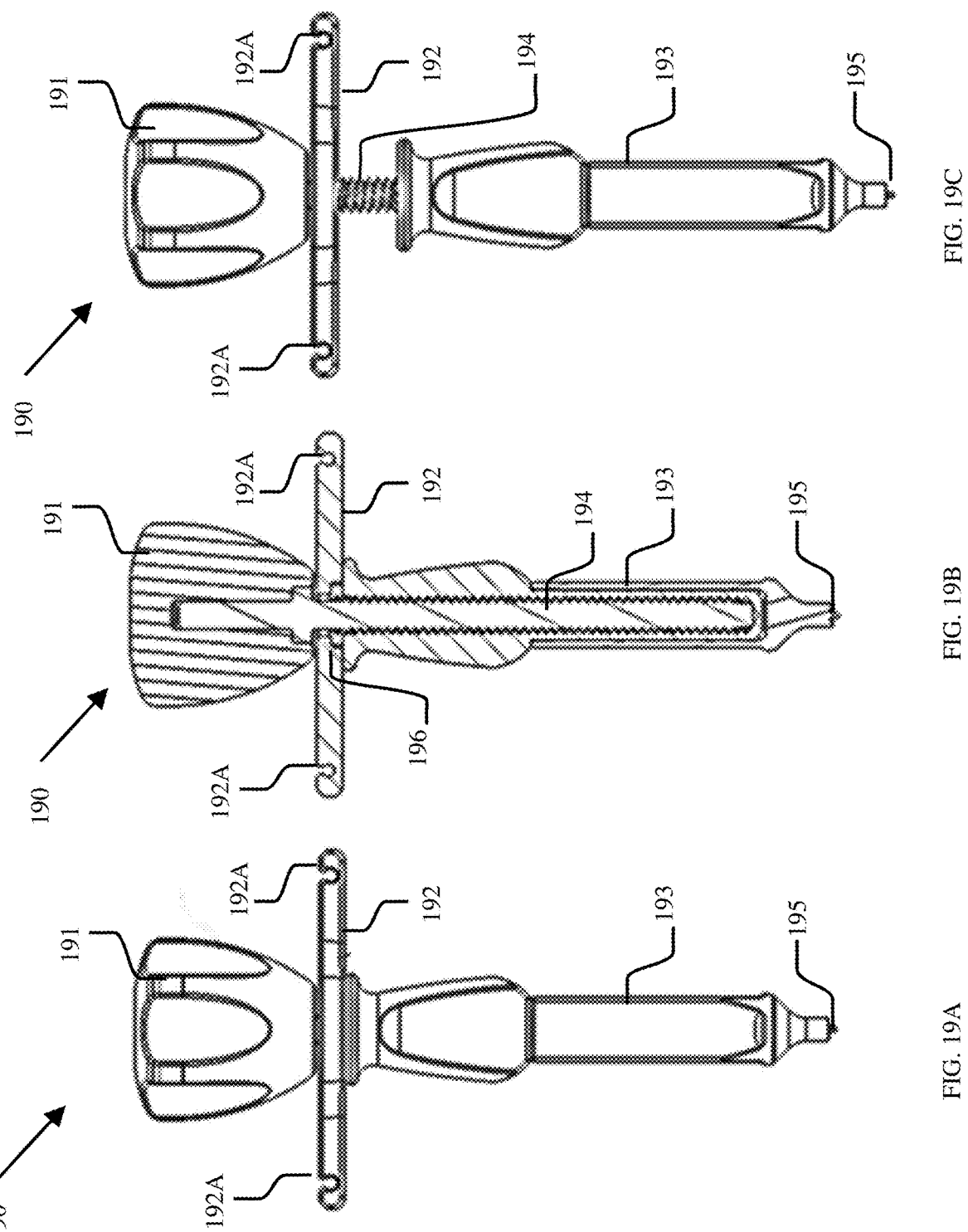
FIG. 19A shows a front-view illustration of an exemplary tightening tool in a collapsed position, per an embodiment herein.
FIG. 19B shows a front cross-sectioned illustration of an exemplary tightening tool in the collapsed position, per an embodiment herein.
FIG. 19C shows a front-view illustration of an exemplary tightening tool in an expanded position, per an embodiment herein.
Figure 20:
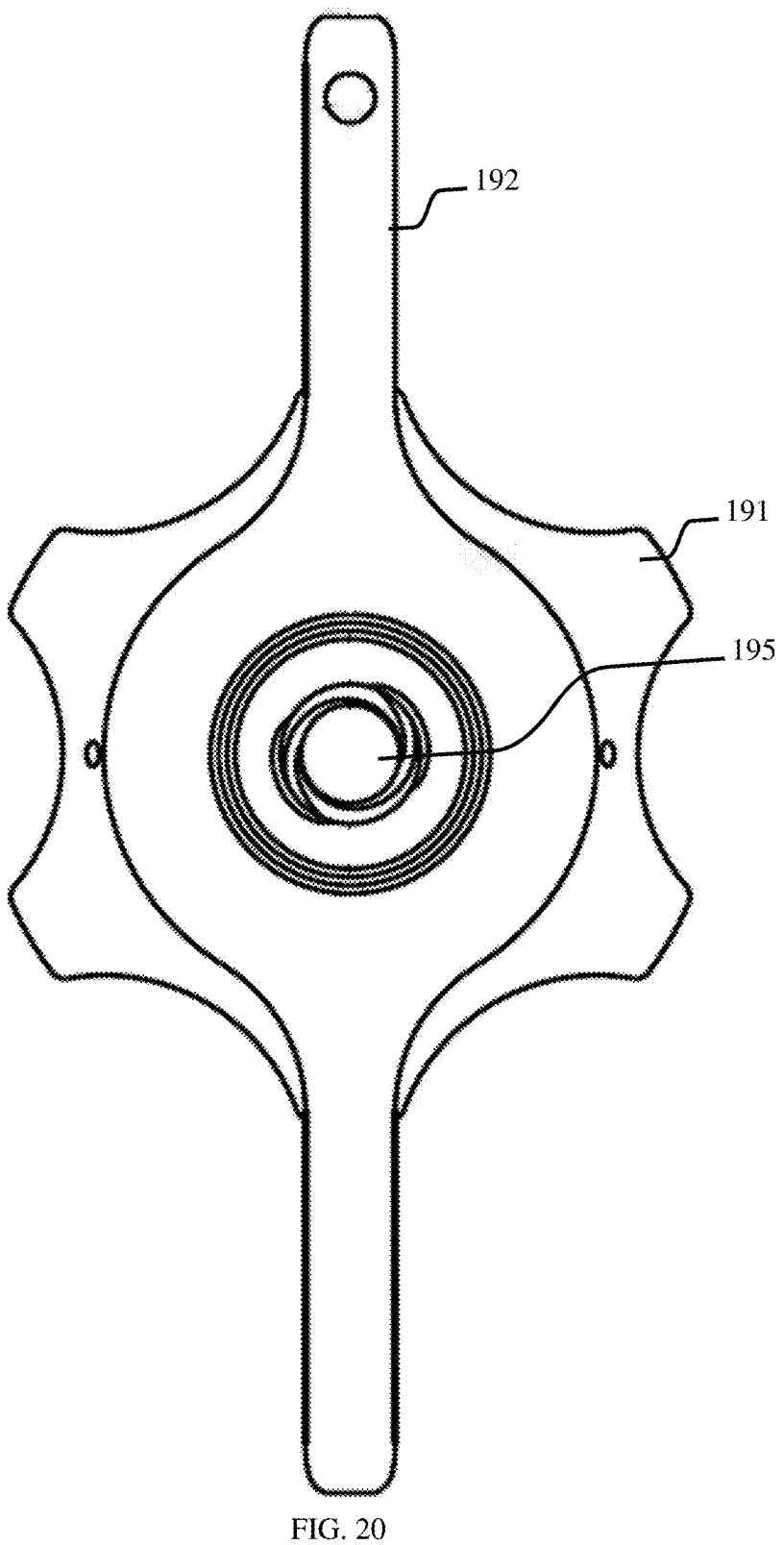
FIG. 20 shows a top-view illustration of an exemplary tightening tool, per an embodiment herein.
Figure 21:
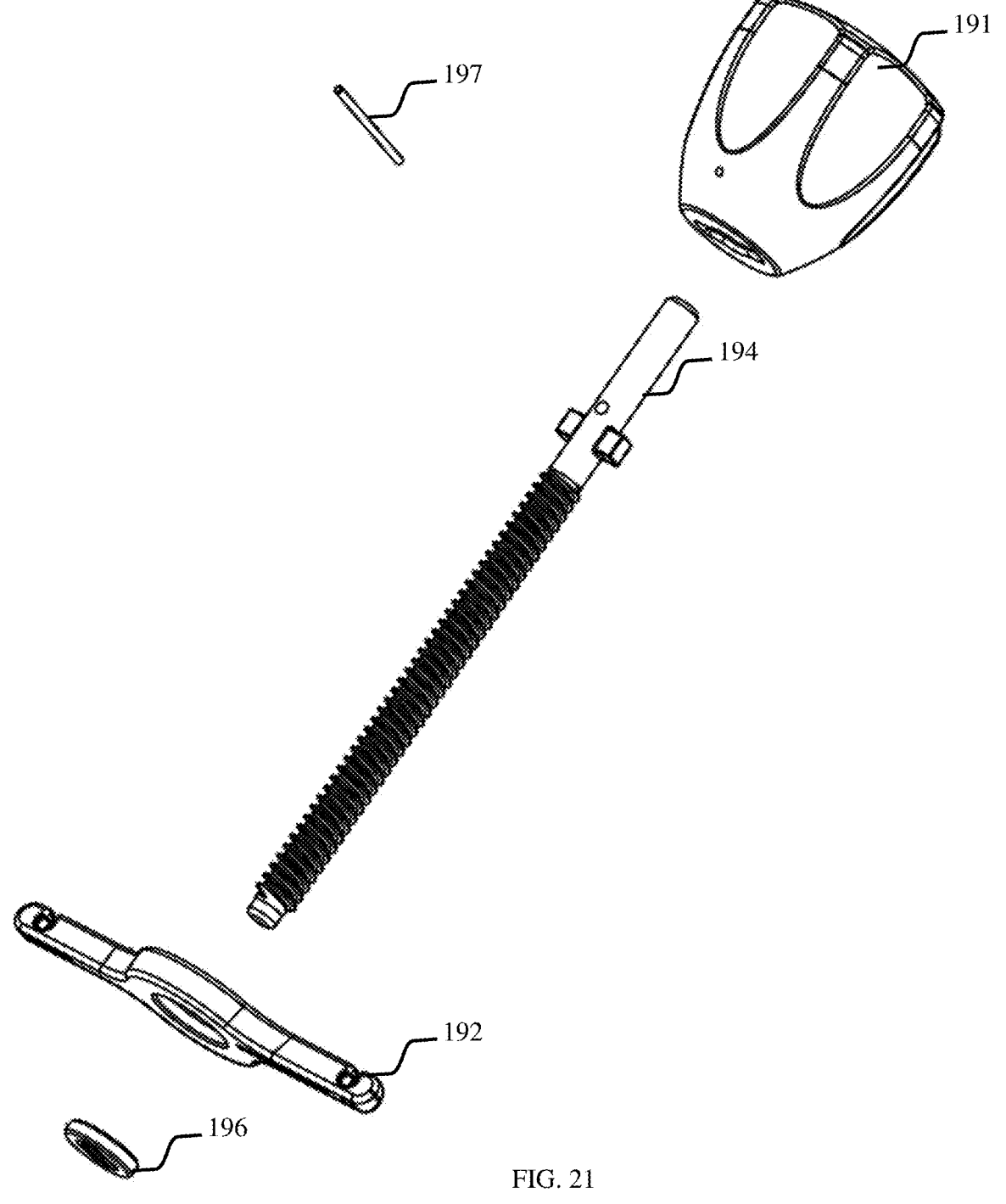
FIG. 21 shows a perspective exploded illustration of an exemplary tightening tool, per an embodiment herein.
Figures 22A, 22B, 22C:
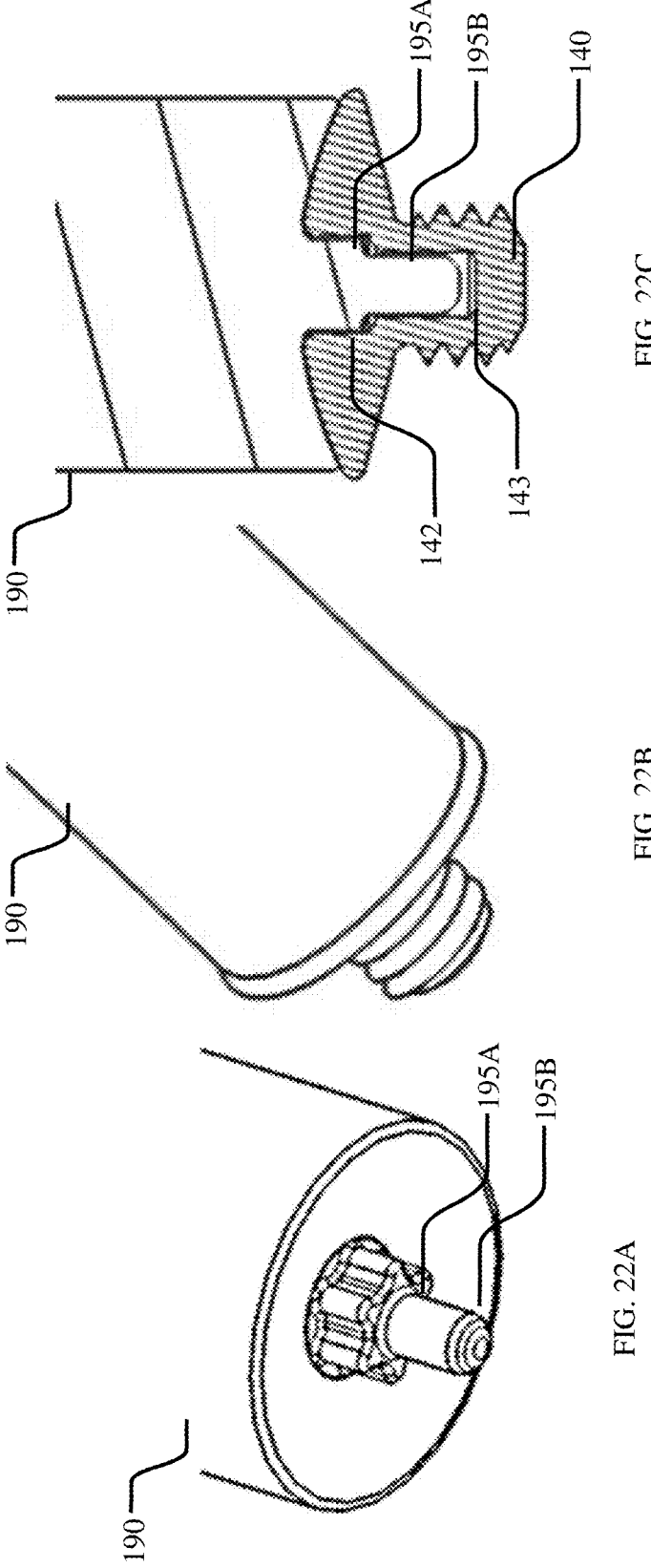
FIG. 22A shows a detailed bottom-left-front perspective illustration of a tensioning feature and an alignment feature of an exemplary tightening tool, per an embodiment herein.
FIG. 22B shows a detailed top-right-front illustration of an exemplary tightening tool engaged with an exemplary lock, per an embodiment herein.
FIG. 22C shows a cross-section illustration of an exemplary tightening tool engaging with the lock, per an embodiment herein.
Figure 23:
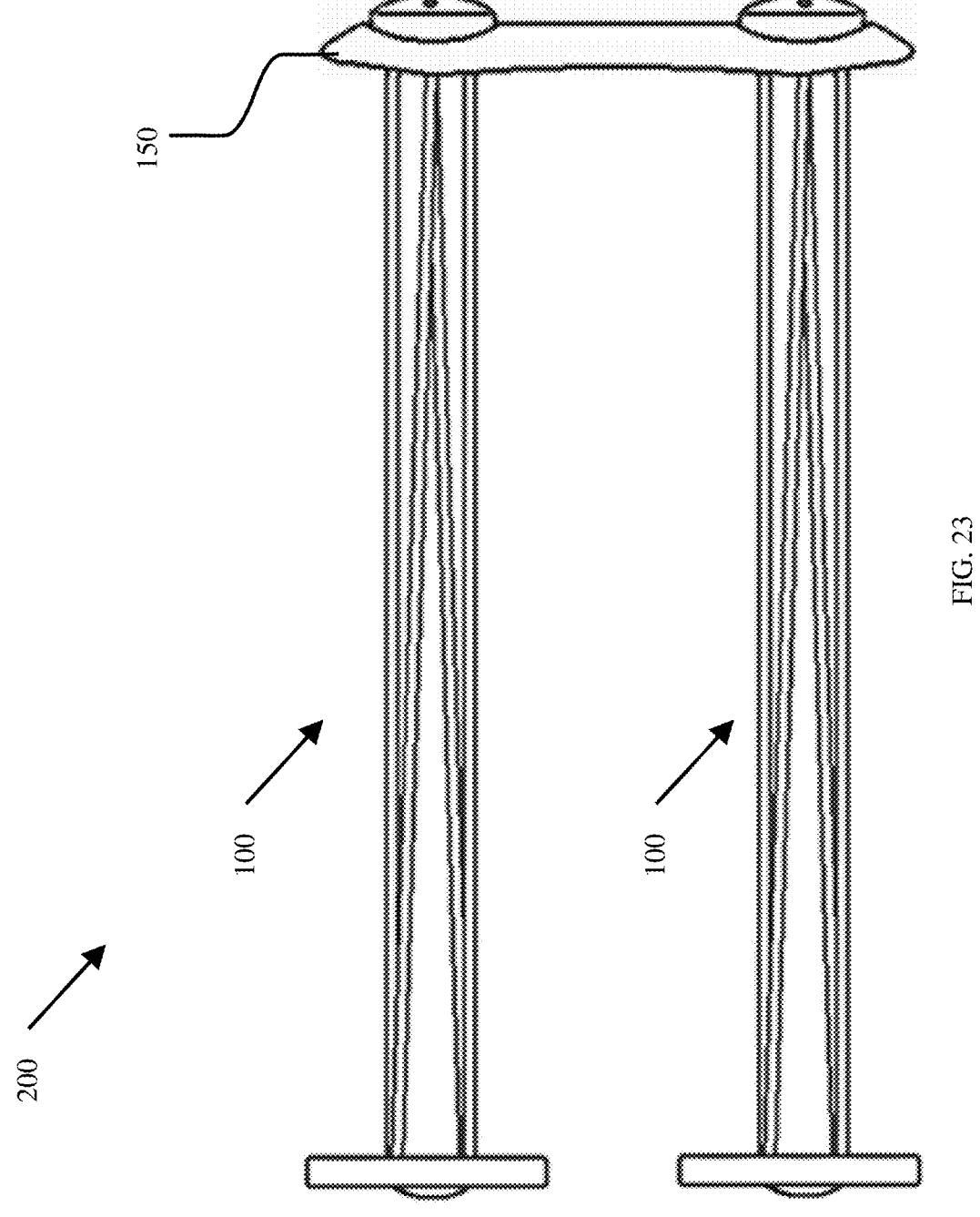
FIG. 23 shows a front-view illustration of an exemplary suture-button assembly comprising two suture-button systems and an insertion plate, per an embodiment herein.
Figure 24:
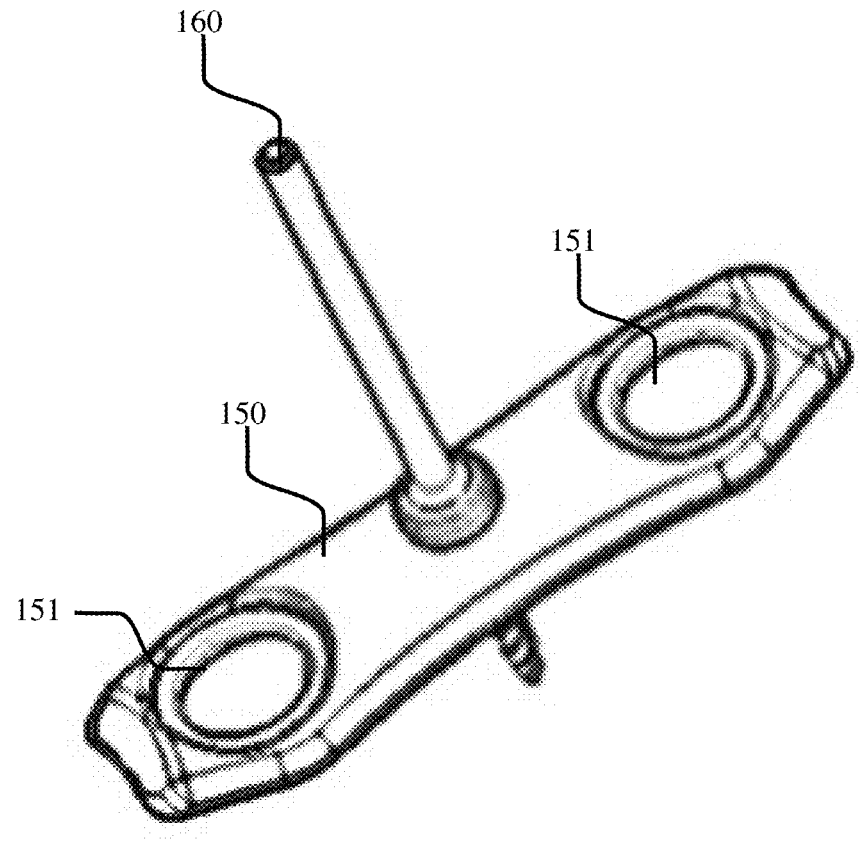
FIG. 24 shows a perspective illustration of an exemplary insertion plate coupled to an exemplary insertion screw, per an embodiment herein.
Figures 25A, 25B, 25C:
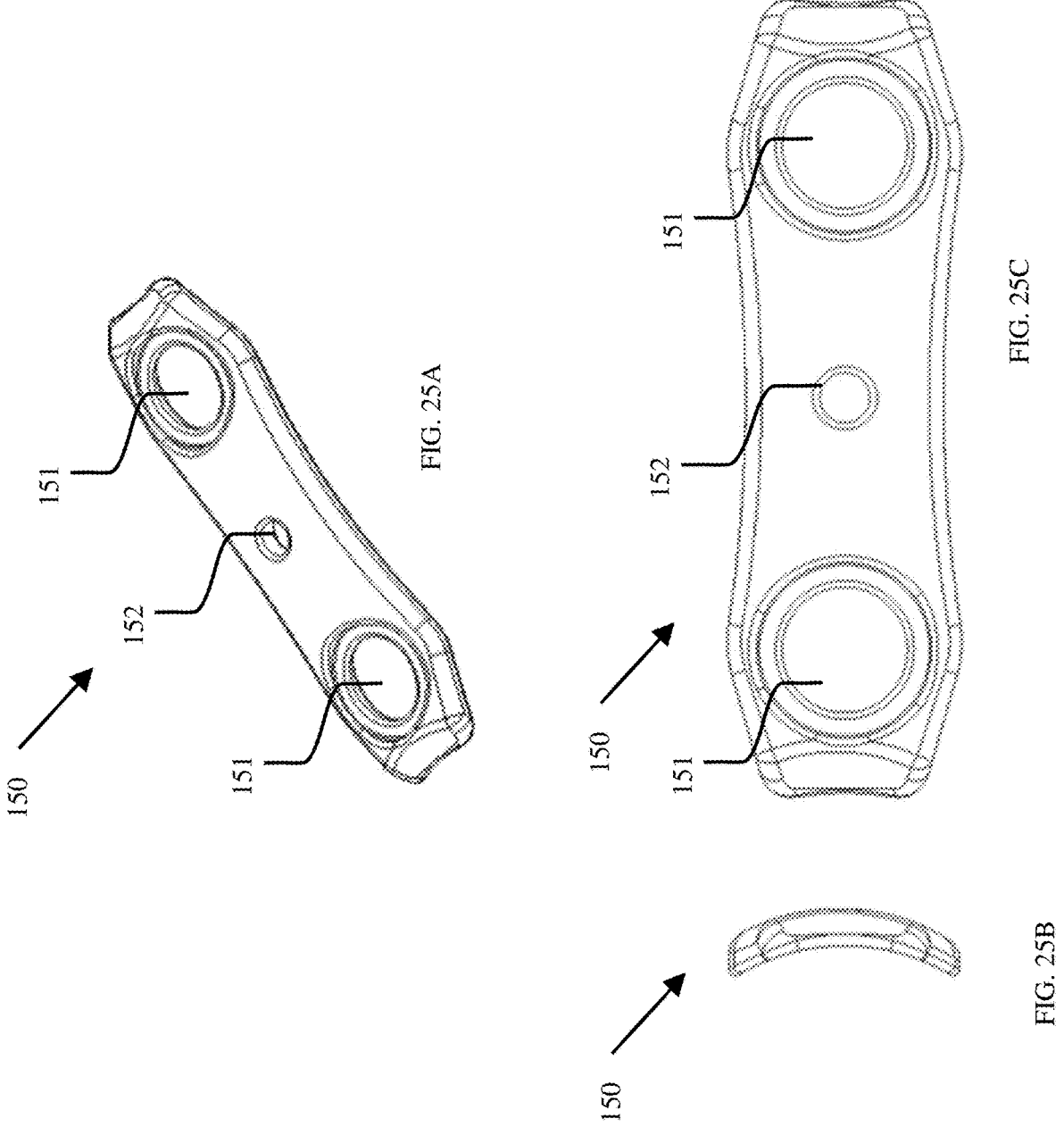
FIG. 25A shows a perspective illustration of the exemplary insertion plate, per an embodiment herein.
FIG. 25B shows a detailed top-right-front illustration of the exemplary insertion plate, per an embodiment herein.
FIG. 25C shows a cross-section illustration of the exemplary insertion plate, per an embodiment herein.
Figures 26A, 26B:
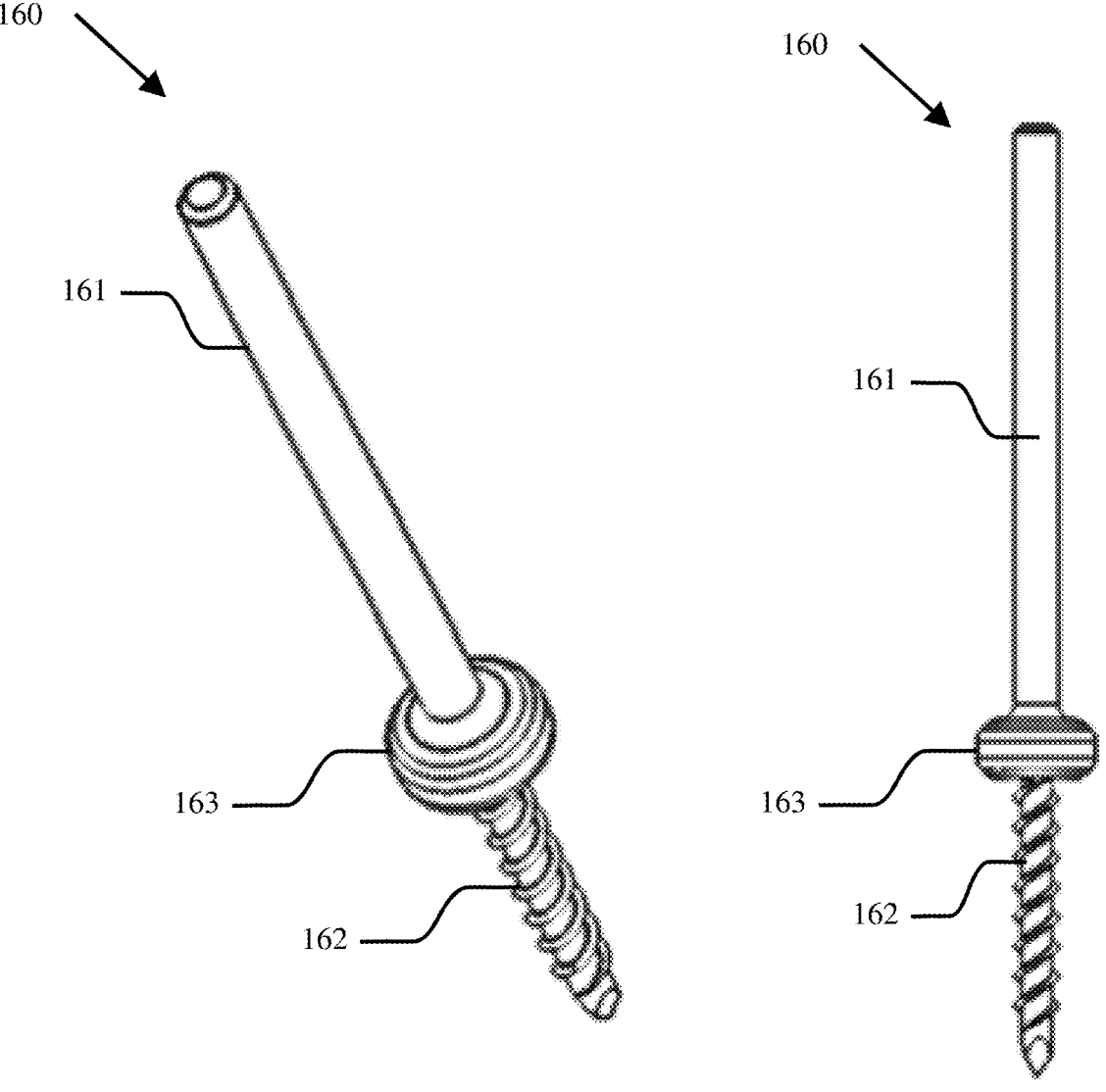
FIG. 26A shows a perspective illustration of an insertion screw, per an embodiment herein.
FIG. 26B shows a front-view illustration of an insertion screw, per an embodiment herein.
Figures 27A, 27B, 27C:
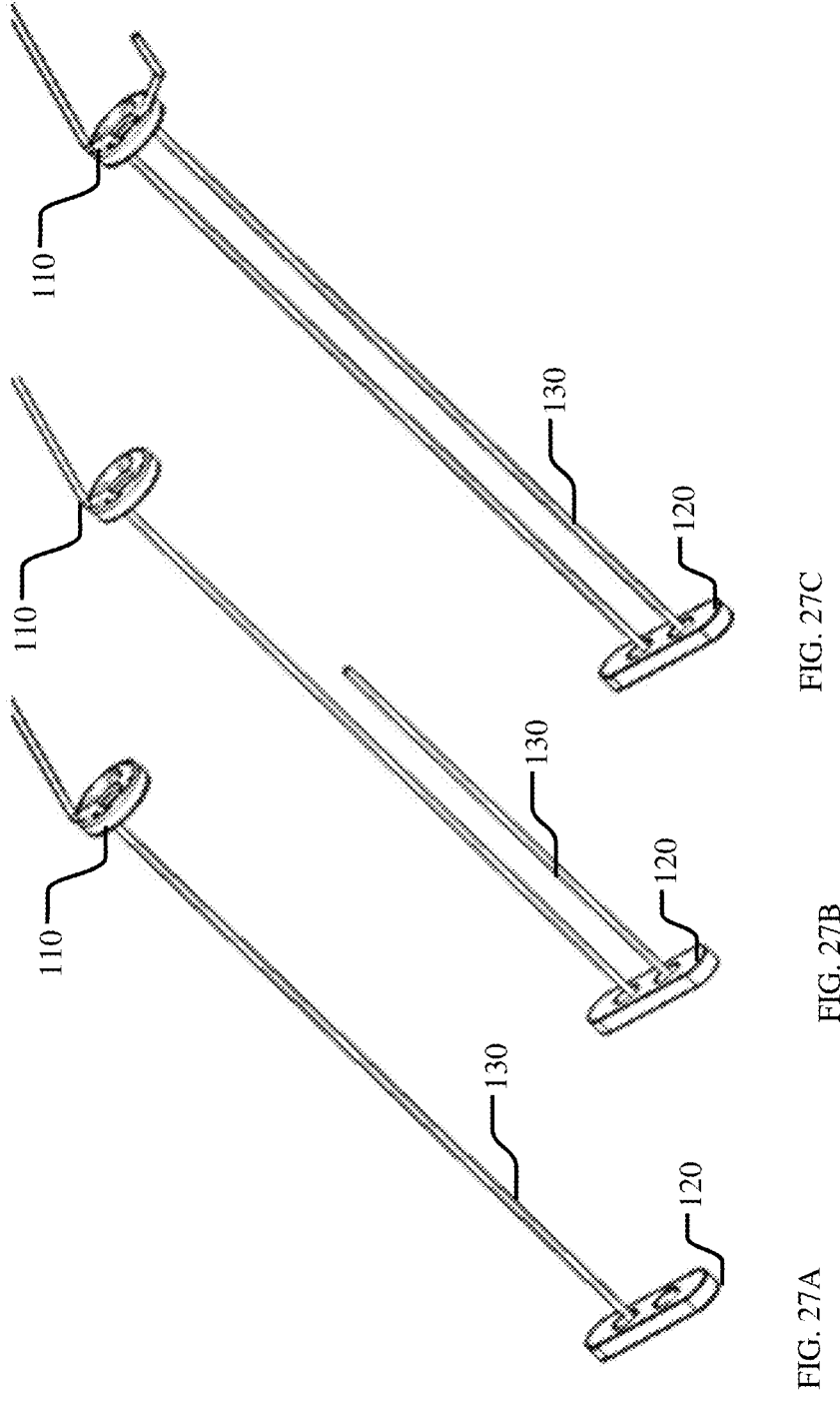
FIG. 27A shows a perspective illustration of inserting a suture strand through a first primary aperture of the primary button, per an embodiment herein.
FIG. 27B shows a perspective illustration of inserting a suture strand through a first and second secondary aperture of the secondary button, per an embodiment herein.
FIG. 27C shows a perspective illustration of inserting a suture strand through a second primary aperture of the primary button, per an embodiment herein.
Figures 28A, 28B, 28C, 28D:
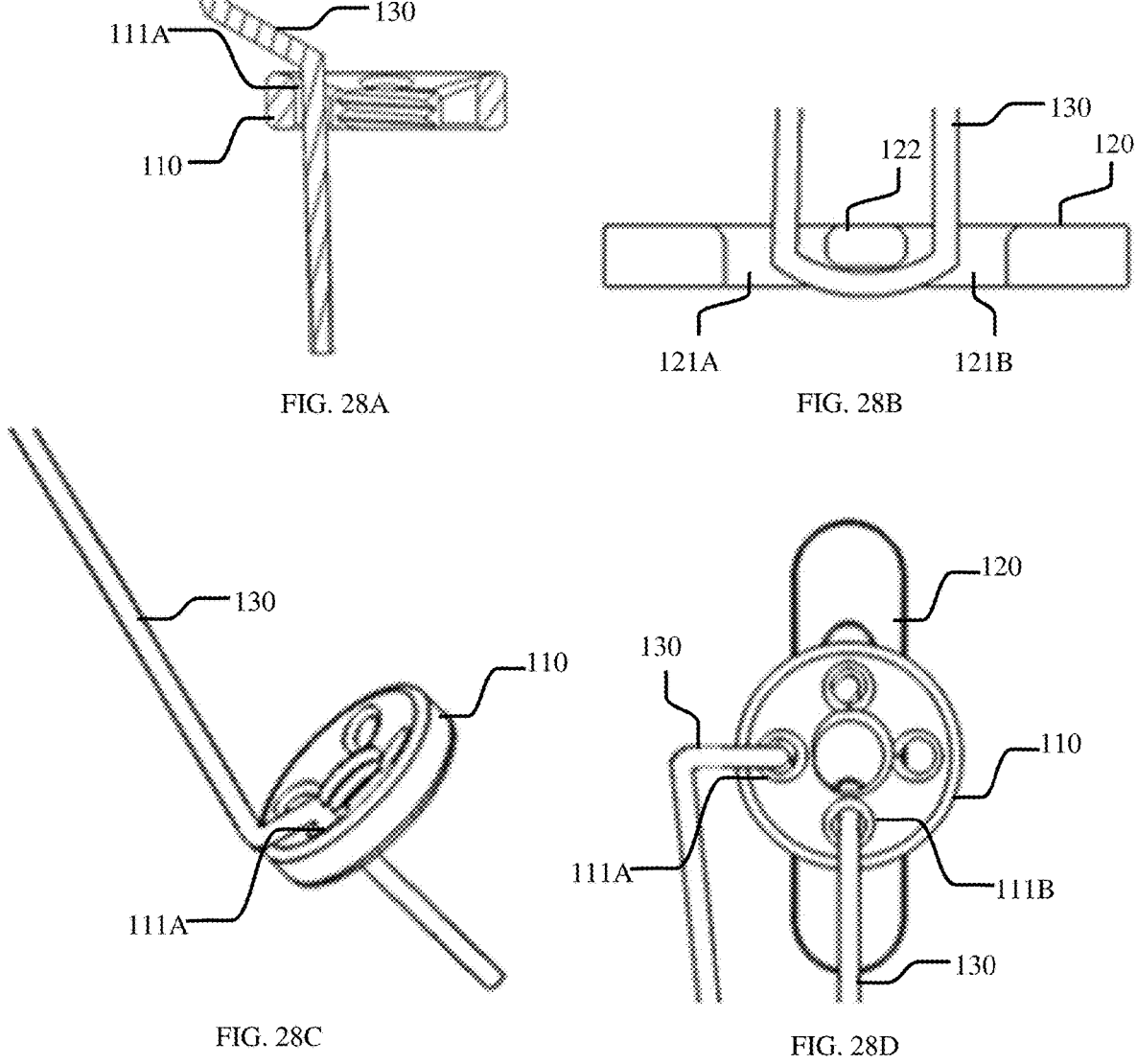
FIG. 28A shows a cross-section illustration of inserting a suture strand through a first primary aperture of the primary button, per an embodiment herein.
FIG. 28B shows a perspective illustration of inserting a suture strand through a first secondary aperture and a second secondary aperture of the secondary button, per an embodiment herein.
FIG. 28C shows a perspective illustration of inserting a suture strand through a first primary aperture of the primary button, per an embodiment herein.
FIG. 28D shows a perspective illustration of inserting a suture strand through a second primary aperture of the primary button, per an embodiment herein.

In some embodiments, per FIG. 13, the system 100 further comprises an insertion suture 210, an insertion needle 220, or both. In some embodiments, the secondary button 120 is attached to the insertion needle 220 via an insertion suture 210. In some embodiments, the insertion needle 220 is configured to be inserted through a hole in a targeted tissue, which then pulls the secondary button 120 therethrough via the insertion suture 210. In some embodiments, pulling the secondary button 120 through the hole in the targeted tissue also pulls the one or more suture strands 130 that is coupled to the secondary button through said hole. In some embodiments, the insertion needle 220 is then disconnected from the secondary button 120 by cutting and removing the insertion suture 210.

In some embodiments, per FIGS. 14A-17D, the system 100 further comprises a lock driver device 180. In some embodiments, the lock driver 180 comprises a driving feature 182 that is configured to rotate the lock 140 relative to the primary button 110. In some embodiments, the driving feature 182 is a male driving feature wherein the driver feature 142 of the lock 140 is a female driver feature. In some embodiments, the driving feature 182 is a female driving feature wherein the driver feature 142 of the lock 140 is a male driver feature. In some embodiments, at least a portion of the driver feature 142 fits within a portion of the driving feature 182. In some embodiments, at least a portion of the driving feature 182 fits within a portion of the driver feature 142. In some embodiments, the lock driver 180 further comprises an aligning feature 183 configured to align the lock driver 180 to the alignment feature 143 of the lock 140. In some embodiments, the aligning feature 183 is configured to align the lock driver 180 to the alignment feature 143 of the lock 140 while the lock driver 180 rotates the lock 140 relative to the primary button 110. In some embodiments, rotating the lock driver 180 in a first direction inserts the secondary threaded portion 141 of the lock 140 distally through the primary threaded portion 113 of the primary button 110. In some embodiments, rotating the lock driver 180 in a second direction opposite the first direction translates the secondary threaded portion 141 of the lock 140 proximally through the primary threaded portion 113 of the primary button 110. In some embodiments, the alignment feature 183 is distal to the driving feature 182. In some embodiments, a maximum outer diameter of the alignment feature 183 is less than a maximum outer diameter of the driving feature 182. As shown, the driver feature 142 comprise a torx driver feature, Alternatively, in some embodiments, the driver feature 142 comprises a Philips driver feature 142, a flathead driver feature 142, a hex driver feature 142, or a square socket feature. In some embodiments, the lock driver 180 enables a greater tightening force than can be applied by hand. In some embodiments, the lock driver 180 enables a more precise and tunable tightening force than can be applied by hand.

In some embodiments, per FIGS. 18-22C, the system 100 further comprises a tightening tool 190. In some embodiments, the tightening tool 190 comprises: a threaded rod 194; a knob 191; a spinner 192, a collar 196, and a handle 193. In some embodiments, the knob 191 is coupled to the threaded rod 194. In some embodiments, the knob 191 is permanently coupled to the threaded rod 194. In some embodiments, the knob 191 is removably coupled to the threaded rod 194. In some embodiments, the knob 191 is coupled to a proximal end of the threaded rod 194. In some embodiments, the collar 196 is coupled to the threaded rod 194. In some embodiments, the collar 196 is coupled to the threaded rod 194 by a fastener, an adhesive, a pin 197, welding or any combination thereof. In some embodiments, the spinner 192 is positioned between the knob 191 and the collar 196. In some embodiments, the spinner 192 comprises an aperture accepting the threaded rod 194. In some embodiments, the spinner 192 further comprises a terminator channel 192A accepting the coupled ends of one or more suture strands 130. In some embodiments, the spinner 192 further comprises a terminator channel 192A accepting the terminator of the suture strand 130. In some embodiments, the spinner 192 comprises 1, 2, 3, 4, 5, 6, or more terminator channels 192A. In some embodiments, the handle 193 comprises a cavity, wherein at least a portion of the cavity comprises a threaded feature configured to couple to the threaded rod 194. In some embodiments, a distal portion of the handle 193 comprises a tensioning feature 195A configured to rotate the driver feature of the lock 140. In some embodiments, the knob 191 is coupled to the proximal end of the threaded rod 194 by a pin 197, an adhesive, a fastener, a press-fit, a weld, or any combination thereof. As shown, the collar 196 is coupled to the threaded rod 194 by a fastener. Alternatively, in some embodiments, the collar 196 is coupled to the threaded rod 194 by a pin, an adhesive, a press-fit, a weld, or any combination thereof. In some embodiments, the lock 140 further comprises the alignment feature 143, and wherein the distal portion of the handle 193 further comprises a tensioning alignment feature 195B that couples to the alignment feature 143. In some embodiments, rotating the knob 191 and the threaded rod 194 in a first direction with respect with to the handle 193 translates the knob 191 and the spinner distally with respect to the handle 193. In some embodiments, rotating the knob 191 and the threaded rod 194 in a second direction opposite the first direction translates the knob 191 and the spinner proximally with respect to the handle 193. In some embodiments, the knob 191 is rotated to translate the spinner 192 proximally or distally, so as to obtain a desired tension of suture strands 130 that are coupled to a terminator channel 192A. In some embodiments, rotating the handle 193 in a first direction inserts the secondary threaded portion 141 of the lock 140 distally through the primary threaded portion 113 of the primary button 110. In some embodiments, rotating the handle 193 in a second direction opposite the first direction translates the secondary threaded portion 141 of the lock 140 proximally through the primary threaded portion 113 of the primary button 110. In some embodiments, the tightening tool 190 enables a greater tightening force than can be applied by hand. In some embodiments, the tightening tool 190 enables a more precise and tunable tightening force than can be applied by hand.

As described herein, for any embodiment described herein, including features described in FIGS. 7-22, primary button 310 may be used instead of or in addition to primary button 110 as part of a suture system.

In some embodiments, applying tension between two ends of each of the one or more suture strands 130 reduces a distance between the primary button 110 and the secondary button 120. In some embodiments, applying tension between two ends of each of the one or more suture strands 130 reduces a distance between the distal surface of the primary button 110 and a proximal surface of the secondary button 110. In some embodiments, applying tension between two ends of each of the one or more suture strands 130 provides a clamping force between the distal surface of the primary button 110 and a proximal surface of the secondary button 110. In some embodiments, applying tension between two ends of each of the one or more suture strands 130 increases a clamping pressure that the primary button 110 and the secondary button 110 apply to a target tissue therebetween. In some embodiments, applying tension between two ends of each of the one or more suture strands 130 increases a clamping pressure that the distal surface of the primary button 110 and the proximal surface secondary button 110 apply to a target tissue therebetween.

In some embodiments, with reference to FIG. 33, applying a tension comprises reducing a distance between primary button 310 and secondary button 120, while pulling or holding the ends (knotted or un-knotted) of one or both of the sutures 330 and 332.

In some embodiments, the target tissue comprises two or more portions of a bone, a muscle tissue, an epithelial tissue, a connective, tissue, a nervous tissue, or any combination thereof. In some embodiments, two or more of the following are clamped together between the primary button 110, 310 and the secondary button 120: a bone, a muscle tissue, an epithelial tissue, a connective, tissue, a nervous tissue, or any combination thereof. In some embodiments, upon tensioning of the suture strands 130, 330, 332, the primary button 110, 310 and the secondary button 120 clamp a bone to: another bone, a muscle tissue, an epithelial tissue, a connective, tissue, a nervous tissue, or any combination thereof. In some embodiments, upon tensioning of the suture strands 130, 330, 332, the primary button 110, 310, and the secondary button 120 clamp a muscle tissue to: bone, another muscle tissue, an epithelial tissue, a connective, tissue, a nervous tissue, or any combination thereof. In some embodiments, upon tensioning of the suture strands 130, 330, 332, the primary button 110, 310, and the secondary button 120 clamp an epithelial tissue to: bone, muscle tissue, another epithelial tissue, a connective, tissue, a nervous tissue, or any combination thereof. In some embodiments, upon tensioning of the suture strands 130, 330, 332, the primary button 110, 310, and the secondary button 120 clamp a connective tissue to: bone, muscle tissue, epithelial tissue, another connective, tissue, a nervous tissue, or any combination thereof. In some embodiments, upon tensioning of the suture strands 130, 330, 332, the primary button 110, 310, and the secondary button 120 clamp a nervous tissue to: bone, muscle tissue, epithelial tissue, connective, tissue, another nervous tissue, or any combination thereof.

Suture-Button Assemblies

Another aspect provided herein, per FIGS. 23-26B, is a suture-button assembly 200 comprising two suture-button systems 100 and an insertion plate 150. In some embodiments, the suture button assembly 200 comprises 2, 3, 4, 5, 6, or more suture button systems 100. As shown, the insertion plate 150 comprises two insertion plate apertures 151, wherein each insertion plate aperture 151 accepts at least one suture strand. Alternatively, in some embodiments, each insertion plate apertures 151 accepts the sutures of 1, 2, 3, 4, 5, 6 or more suture button assemblies. In some embodiments, the plurality of insertion plate apertures 151 comprises 2, 3, 4, 5, 6, or more insertion plate apertures 151, wherein each insertion plate aperture 151 accepts the sutures of one suture button assembly. In some embodiments, each insertion plate apertures 151 accepts 1, 2, 3, 4, 5, 6 or more sutures. In some embodiments, the plurality of insertion plate apertures 151 In some embodiments, a screw hole 152 is positioned between two of the plurality of insertion plate apertures 151. In some embodiments, the screw hole 152 is positioned equidistant between two of the plurality of insertion plate apertures 151.

In some embodiments, the assembly further comprises an insertion screw 160. In some embodiments, insertion screw 160 is configured to be removably coupled with the screw hole 152. In some embodiments, the insertion screw 160 comprises a first portion 161, a second portion 162 configured to attach to a bone of a patient, and a third portion 163 having length and/or diameter greater than a greatest length or diameter of the screw hole 152. In some embodiments, the third portion 163 prevents the first portion 161 from passing through the screw hole 152 after the second portion 162 has been inserted therethrough. In some embodiments, the second portion comprises a threaded feature configured to attach to the bone of the patient.

In some embodiments, for any suture-button assembly described herein, including FIGS. 23-26B, one or more of the suture button systems 100 comprises a primary button 310 instead of or in addition to primary button 110.

Method of Assembling a First Suture Button System

Another aspect provided herein is a method of assembling a first suture button system 100. In some embodiments, the method comprises: providing a first suture-button system 100 wherein the primary button 110 comprises a first primary aperture 111 and a second primary aperture 111, wherein the secondary button 120 comprises a first secondary aperture 121 and a second secondary aperture 121, and wherein the first suture button system comprises one suture strand 130. In some embodiments, the method comprises inserting the suture strand 130 through the first primary aperture 111, inserting the one suture strand 130 through the first secondary aperture 121, inserting the one suture strand 130 through the second secondary aperture 121, and inserting the one suture strand 130 through the second primary aperture 111. In some embodiments, one or more of the steps of inserting the suture strand 130 through the first primary aperture 111, through the first secondary aperture 121, through the second secondary aperture 121, and through the second primary aperture 111 are performed simultaneously. In some embodiments, the method further comprises coupling the two ends of the suture strand 130 together. In some embodiments, the method further comprises coupling the two ends of the suture strand 130 by tying the two ends of the suture strand 130 together. In some embodiments, the method further comprises coupling the two ends of the suture strand 130 with a terminator.

In some embodiments, the method further comprises inserting the secondary button 120 through a hole in a proximal surface of a bone or tissue of a patient, and tightening the suture such that the primary button 110 and the secondary button 120 are tightly pressed against opposing surfaces of the bone. In some embodiments, the secondary button 120 is inserted through a bone or tissue hole extending through at least one bone. In some embodiments, the bone or tissue hole is a tunnel, channel, passageway, or any combination thereof. In some embodiments, the secondary button 120 is attached to an insertion needle 220 via one or more insertion suture 210 loops. In some embodiments, the insertion suture 210 loops may be formed by passing an insertion suture 210 through one or more secondary apertures 121 in the secondary button 120 and attaching both free ends of the one or more insertion suture strands 210 to the insertion needle 220. In some embodiments, the free ends of the one or more insertion suture strands 210 are attached to the insertion needle 220 via crimping. In some embodiments, the insertion needle 220 may be inserted through said bone or tissue hole on a first side of the bone or tissue, and received on a second side, such that the secondary button 120 is pulled through the hole in its most narrow configuration. In some embodiments, the secondary button 120, after passing through the bone or tissue hole in its most narrow configuration, is then pivoted such that it lies flat against the bone or tissue. In some embodiments, the secondary button 120 lies against the bone or tissue on its length 120A. In some embodiments, the primary button 110 and secondary button 120 are disposed on either side of the bone or tissue hole with the suture 130 extending through the bone or tissue hole. In some embodiments, the insertion needle 220 is disconnected from the secondary button by cutting and removing the insertion suture 210. In some embodiments, the suture strand 130 is tightened, such that the primary and secondary buttons apply a clamping force or pressure on a first and second side of a bone or tissue.

As described herein, tightening the suture includes applying a tension to the coupled ends of the suture 130. In some embodiments, pulling the coupled ends of the suture 130 applies tension to the suture. In some embodiments, pulling the coupled ends of the suture 130 in a proximal direction applies tension to the suture. In some embodiments, the tightening is performed by hand. In some embodiments, the tightening is performed by the lock driver described herein. In some embodiments, the tightening is performed by rotating the tightening tool 190 herein. In some embodiments, the tightening comprises inserting the suture strand loop 130 within the terminator channels 192A of the spinner 192, coupling the tensioning feature 195A and the driver feature of the lock 140, and rotating the knob 191 with respect to the handle 193. In some embodiments, the tightening comprises inserting the suture strand loop 130 within the terminator channels 192A of the spinner 192, coupling the tensioning feature 195A and the driver feature of the lock 140, rotating the knob 191 with respect to the handle 193, and rotating the tightening tool 190 with respect to the driving feature of the lock 140. In some embodiments, rotating the knob 191 in a first direction translates the spinner 192 and terminator channels 192A proximally from the handle 193, thereby tightening the suture strand 130. In some embodiments, rotating the knob 191 in a second direction translates the spinner 192 and terminator channels 192A distally to the handle 193, thereby loosening the suture strand 130, and decreasing the tension. In some embodiments, once the desired tension is reached the lock 140 is tightened against the primary button 110 such that the suture is locked in place therebetween. In some embodiments, the lock 140 is loosened against the primary button 110 to enable readjustment of the tension of the suture strand, wherein the lock 140 is subsequently tightened against the primary button 110 once the desired tension is reached. In some embodiments, the method further comprises trimming the loose ends of the suture.

Method of Assembling a Second Suture Button System

Further provided herein, per FIGS. 27A-29B, is a method of assembling a second suture button system 100. In some embodiments, the method comprises providing a second suture-button system 100 wherein the primary button 110 comprises a first primary aperture 111, a second primary aperture 111, a third primary aperture 111, and a fourth primary aperture 111, the secondary button 120 comprises a first secondary aperture 121 and a second secondary aperture 121, and the one or more a suture strands 130 consists of a first suture strand 130 and a second suture strand 130.

In some embodiments, the method comprises: inserting the first suture strand 130 through the first primary aperture 111; inserting the first suture strand 130 through the first secondary aperture 121; inserting the first suture strand 130 through the second secondary aperture 121; inserting the first suture strand 130 through the second primary aperture 111; inserting the second suture strand 130 through the third primary aperture 111; inserting the second suture strand 130 through the first secondary aperture 121; inserting the second suture strand 130 through the second secondary aperture 121; and inserting the second suture strand 130 through the fourth primary aperture 111. In some embodiments, one or more of the inserting the first suture strand 130 through the first primary aperture 111, inserting the first suture strand 130 through the first secondary aperture 121, inserting the first suture strand 130 through the second secondary aperture 121, inserting the first suture strand 130 through the second primary aperture 111, inserting the second suture strand 130 through the third primary aperture 111, inserting the second suture strand 130 through the first secondary aperture 121, inserting the second suture strand 130 through the second secondary aperture 121, and inserting the second suture strand 130 through the fourth primary aperture 111 are performed simultaneously.

In some embodiments, the method comprises: inserting the first suture strand 130 through the first primary aperture 111; inserting the first suture strand 130 through the first secondary aperture 121; inserting the first suture strand 130 through the second secondary aperture 121; inserting the first suture strand 130 through the second primary aperture 111; inserting the second suture strand 130 through the third primary aperture 111; inserting the second suture strand 130 through the second secondary aperture 121; inserting the second suture strand 130 through the first secondary aperture 121; and inserting the second suture strand 130 through the fourth primary aperture 111. In some embodiments, one or more of the inserting the first suture strand 130 through the first primary aperture 111, inserting the first suture strand 130 through the first secondary aperture 121, inserting the first suture strand 130 through the second secondary aperture 121, inserting the first suture strand 130 through the second primary aperture 111, inserting the second suture strand 130 through the third primary aperture 111, inserting the second suture strand 130 through the second secondary aperture 121, inserting the second suture strand 130 through the first secondary aperture 121, and inserting the second suture strand 130 through the fourth primary aperture 111 are performed simultaneously.

Figures 29A, 29B:
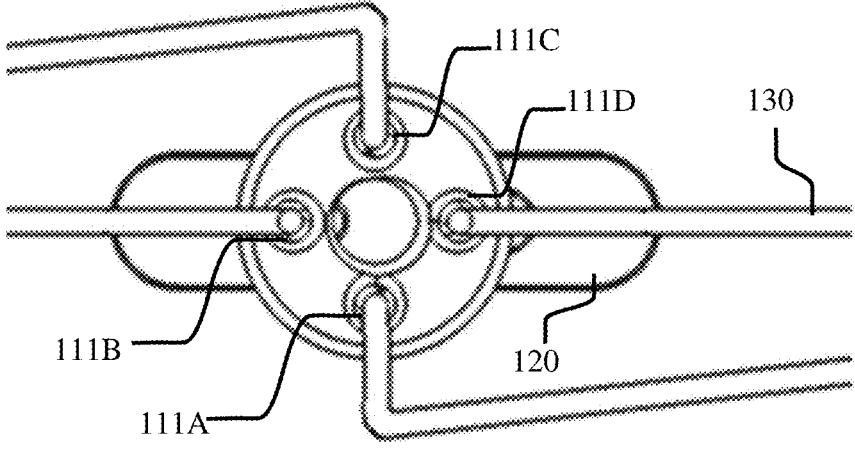
FIG. 29A shows a cross-section illustration of inserting a first and second suture strand through the respective apertures of the primary button, per an embodiment herein.
FIG. 29B shows a perspective illustration of a lock securing a first and second suture strand inserted through the respective apertures of the primary button, per an embodiment herein.

Per FIG. 29A, both the first primary aperture 111 and the third primary aperture 111 are adjacent to the second primary aperture 111 and the fourth primary aperture 111. Further as shown, the first primary aperture 111, the second primary aperture 111, the third primary aperture 111 and the fourth primary aperture 111 are arrayed sequentially in a clockwise direction about the primary button 110. Alternatively, in some embodiments, both the first primary aperture 111 and the second primary aperture 111 are adjacent to the third primary aperture 111 and the fourth primary aperture 111. In some embodiments, the first primary aperture 111, the third primary aperture 111, the second primary aperture 111 and the fourth primary aperture 111 are arrayed sequentially in a clockwise direction about the primary button 110. In some embodiments, the first primary aperture 111, the third primary aperture 111, the second primary aperture 111 and the fourth primary aperture 111 are arrayed sequentially in a counter-clockwise direction about the primary button 110. In some embodiments, the first primary aperture 111, the second primary aperture 111, the third primary aperture 111 and the fourth primary aperture 111 are arrayed sequentially in a counter-clockwise direction about the primary button 110.

In some embodiments, the method further comprises inserting the secondary button 120 through a hole in a bone or tissue of a patient, as described herein, and tightening the sutures such that the primary button 110 and the secondary button 120 are tightly pressed against respective surfaces of the bone or tissue. In some embodiments, the tightening is performed by hand. In some embodiments, the tightening is performed by the lock driver as described herein. In some embodiments, the tightening is performed by the tightening tool as described herein.

In some embodiments, once the desired tension is reached, the lock 140 is tightened against the primary button 110 such that the sutures are locked in place therebetween. In some embodiments, the method further comprises trimming the loose ends of the sutures.

Method of Assembling a Third Suture Button System

With reference to FIGS. 30-33, further provided herein is a method of assembling a third suture button system 100. In some embodiments, the method comprises providing a third suture-button system 100 wherein the primary button 310 comprises a first plurality of primary apertures 311, a second plurality of primary apertures 315, the secondary button 120 comprises a first secondary aperture 121 and a second secondary aperture 121, and one or more a suture strands (e.g., 330 and 332). In some embodiments, the first plurality of primary apertures 311 comprises a primary aperture 311a, a second primary aperture 311b, a third primary aperture 311c, and a fourth primary aperture 311d. In some embodiments, the second plurality of primary apertures 315 comprises a fifth primary aperture 315a, a sixth primary aperture 315b, a seventh primary aperture 315c, and an eighth primary aperture 315d.

In some embodiments, the method comprises: inserting the first suture strand 330 through the first primary aperture 311a then through the third primary aperture 311c; inserting the first suture strand 330 through the first secondary aperture 121; inserting the first suture strand 330 through the second secondary aperture 121; inserting the first suture strand 330 through the second primary aperture 311b and then through the fourth primary aperture 311d; inserting the second suture strand 332 through the fifth primary aperture 315*a* and then the seventh primary aperture 315*c*; inserting the second suture strand 332 through the first secondary aperture 121; inserting the second suture strand 332 through the second secondary aperture 121; and inserting the second suture strand 332 through the sixth primary aperture 315*f* and then through the eight primary aperture 315*h*. In some embodiments, inserting the first and/or second suture strand through the respective primary apertures can occur in any sequential order. For example, in some embodiments, the first suture strand 330 is inserted through the third primary aperture 311*c* and then then first primary aperture 311*a*. In some embodiments, the first suture strand 330 is inserted through the second and fourth primary apertures before being inserted through the first and third primary apertures. In some embodiments, the first and second sutures are inserted through the respective apertures simultaneously, or in any sequential order.

In some embodiments, the method comprises: inserting a first end of the first suture strand 330 through the first secondary aperture 121; inserting the first end of the first suture strand 330 through the first primary aperture 311*a* then through the third primary aperture 311*c* (or vice versa as described herein); then inserting a second end of the first suture strand 330 through the second secondary aperture 121; inserting the second end of the first suture strand 330 through the second primary aperture 311*b* and then through the fourth primary aperture 311*d* (or vice versa as described herein); inserting a first end of the second suture strand 332 through the first (or second) secondary aperture 121; inserting the first end of the second suture strand 332 through the fifth primary aperture 315*a* and then the seventh primary aperture 315*c* (or vice versa as described herein); inserting a second end of the second suture strand 332 through the second (or first) secondary aperture 121; and inserting the second end of the second suture strand 332 through the sixth primary aperture 315*b* and then through the eighth primary aperture 315*d* (or vice versa as described herein). In some embodiments, inserting the first and/or second ends of the first and/or second suture strands 330, 332 through the respective apertures can occur in any sequential order (as described herein). In some embodiments, the first and/or second ends of the first and/or second suture strands 330, 332 are inserted through the respective apertures simultaneously, or in any sequential order.

In some embodiments, the method further comprises knotting the ends for one or both suture strands 330, 332.

In some embodiments, as described herein, the method further comprises inserting the secondary button 120 through a hole in a bone or tissue of a patient, as described herein, and tightening the sutures such that the primary button 310 and the secondary button 120 are tightly pressed against respective surfaces of the bone or tissue. In some embodiments, the tightening is performed by hand. In some embodiments, the tightening is performed by the lock driver as described herein. In some embodiments, the tightening is performed by the tightening tool as described herein. In some embodiments, for example, the ends of one or both suture strands 330, 332 is pulled or held as the sutures are tightened.

In some embodiments, once the desired tension is reached, the lock 140 is inserted and/or tightened against the primary button 310 such that the sutures are locked in place therebetween. In some embodiments, the method further comprises trimming the loose ends of the sutures.

Method of Assembling a Suture Button Assembly

Provided herein, per FIGS. 23-26B are methods for assembling a suture button assembly 200. In some embodiments, the method comprises inserting the primary button 110 of a first suture button system 100 into a first insertion plate aperture 151 of the insertion plate 150, and inserting the primary button 110 of a second suture button system 100 into a second insertion plate aperture 151 of the insertion plate 150. In some embodiments, the method comprises inserting the secondary button 120 of a first suture button system 100 into a first insertion plate aperture 151 of the insertion plate 150, and inserting the secondary button 120 of a second suture button system 100 into a second insertion plate aperture 151 of the insertion plate 150. In some embodiments, the method comprises inserting the primary button 110 of a first suture button system 100 into a first insertion plate aperture 151 of the insertion plate 150, and inserting the secondary button 120 of a second suture button system 100 into a second insertion plate aperture 151 of the insertion plate 150.

In some embodiments, the method comprises inserting each of a plurality of suture strands 130 through one or more of the secondary apertures 121 of the secondary button 120 of a first suture button system 100, inserting each of a plurality of suture strands 130 through one or more of the secondary apertures 121 of the secondary button 120 of a second suture button system 100, inserting each of a plurality of suture strands 130 of the first suture button system 100 through a first insertion plate aperture 151 of the insertion plate 150, inserting each of a plurality of suture strands 130 of the second suture button system 100 through a second insertion plate aperture 151 of the insertion plate 150, inserting each of a plurality of suture strands 130 through one or more of the primary apertures 111 of the primary button 110 of a first suture button system 100, and inserting each of a plurality of suture strands 130 through one or more of the primary apertures 111 of the primary button 110 of a second suture button system 100.

In some embodiments, the method further comprises inserting the insertion screw 160 into the insertion hole 152 of the insertion plate 150. In some embodiments, the method further comprises screwing the insertion screw 160 into a bone or tissue of a patient. In some embodiments, screwing the insertion screw 160 into a bone or tissue of a patient temporarily fixates the plate to the bone or tissue of the patient while the suture-button system is deployed.

As described herein, in some embodiments, for FIGS. 23-26B, primary button 310 may be used instead of or in addition to primary button 110, using one or more suture strands (e.g., 330, 332 as described herein).

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the term "generally" refers to a geometric relationship between two or more elements within tolerances of 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Other Exemplary Embodiments

One aspect provided herein is a suture-button system comprising: a suture strand; a primary button having a plurality of primary apertures and a primary threaded portion, wherein the suture strand is inserted through a first and second primary aperture of the plurality of primary apertures; a secondary button having a plurality of secondary apertures, wherein the suture strand is inserted through a first and second secondary aperture of the plurality of secondary apertures, such that at least one targeted tissue of a subject is clamped between a distal surface of the primary button and a proximal surface of the secondary button upon applying a tension to the suture strand; and a lock having a secondary threaded portion, wherein the secondary threaded portion is removably coupled to the primary threaded portion, wherein coupling the secondary threaded portion of the lock to the threaded portion prevents the suture strand from translating through the plurality of primary apertures, thereby securing the clamping of the targeted tissue.

In some embodiments, the plurality of primary apertures comprises 2, 3, 4, or 5 primary apertures. In some embodiments, the plurality of primary apertures are equally spaced on the primary button. In some embodiments, the plurality of primary apertures are equally spaced on the primary button in a circular array. In some embodiments, the plurality of primary apertures are equally spaced on the primary button in a circular array about the primary threaded portion. In some embodiments, the plurality of primary apertures are equally spaced on the primary button in a circular array about a center axis of the secondary button. In some embodiments, a proximal surface of the primary button comprises a countersink. In some embodiments, the primary threaded portion comprises a female threaded portion. In some embodiments, the secondary threaded portion comprises a male threaded portion. In some embodiments, the primary threaded portion comprises a male threaded portion. In some embodiments, the secondary threaded portion comprises a female threaded portion. In some embodiments, the plurality of secondary apertures comprises 2, 3, 4, or 5 secondary apertures. In some embodiments, a distal surface of the secondary button comprises a channel connecting two or more of the plurality of secondary apertures. In some embodiments, one or more edges of the secondary button are rounded or chamfered. In some embodiments, an aspect ratio between the length and width of the secondary button is about 1:1 to about 4:1. In some embodiments, the lock comprises a head and wherein the secondary threaded portion extends from the head. In some embodiments, a distal surface of the head is tapered outwards from a center axis of the lock. In some embodiments, the distal surface of the head is tapered outwards from a center axis of the lock by about 20° to about 89°. In some embodiments, the suture strand is a #1 size suture, a #2 size suture, a #3 size suture, a #4 size suture, a #5 size suture, a #6 size suture, or a #7 size suture.

In some embodiments, the suture strand has a length of about 100 mm to about 1,200 mm. In some embodiments, the system comprises 2, 3, 4, 5, 6 or more suture strands. In some embodiments, the system comprises a first suture strand and a second suture strand, wherein at least a portion of the first suture strand passes within at least a portion of the second suture strand to form a suture bundle. In some embodiments, the portion of the first suture strand that passes within the second suture strand is a mesial portion of the first suture. In some embodiments, the portion of the second suture strand through which the first suture strand passes is a mesial portion of the second suture. In some embodiments, the lock comprises a driver feature, an alignment feature, or both. In some embodiments, the driver feature is opposite the secondary threaded portion. In some embodiments, the driver feature and the alignment feature are generally concentric. In some embodiments, the driver feature is proximal to the alignment feature. In some embodiments, a maximum inner diameter of the driver feature is greater than a maximum inner diameter of the alignment feature. In some embodiments, the driver feature comprises a Philips driver feature, a flathead driver feature, a torx driver feature, a hex driver feature, or a square socket feature. In some embodiments, the alignment feature has a cross sectional shape comprising a circle, a triangle, a square, a pentagon, a hexagon, an octagon, or any combination thereof. In some embodiments, the system further comprises a lock driver comprising a driving feature that is configured to rotate the lock relative to the primary button. In some embodiments, the lock driver further comprises an aligning feature configured to align the lock driver to the alignment feature of the lock. In some embodiments, the alignment feature is distal to the driving feature. In some embodiments, at least a portion of the lock extends beyond a distal face of the primary button when the primary button is coupled to the lock. In some embodiments, a distal face of the primary button extends beyond a distal face of the lock when the primary button is coupled to the lock. In some embodiments, wherein at least one end of the suture strand is coupled to a terminator. In some embodiments: the system comprises two suture strands, wherein the plurality of primary apertures comprises four primary apertures; the plurality of secondary apertures comprises two secondary apertures; a first suture strand is inserted through a first primary aperture, through a first secondary aperture, through a second secondary aperture, and through a second primary aperture; and a second suture strand is inserted through a third primary aperture, through the first secondary aperture, through the second secondary aperture, and through a fourth primary aperture. In some embodiments: the system comprises two suture strands, wherein the plurality of primary apertures comprises four primary apertures; the plurality of secondary apertures comprises two secondary apertures; a first suture strand is inserted through a first primary aperture, through a first secondary aperture, through a second secondary aperture, and through a second primary aperture; and a second suture strand is inserted through a third primary aperture, through the second secondary aperture, through the first secondary aperture, and through a fourth primary aperture; In some embodiments, the first primary aperture and the second primary aperture are adjacent. In some embodiments, the first primary aperture and the second primary aperture are nonadjacent. In some embodiments, the system further comprises a tightening tool comprising: a threaded rod; a knob coupled to a proximal end of the threaded rod; a collar coupled to the threaded rod; an arm spinner between the knob and the collar, wherein the arm spinner comprises an aperture accepting the threaded rod; and a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driving feature of the lock. In some embodiments, the arm spinner further comprises a terminator channel accepting the terminator. In some embodiments, the arm spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature. In some embodiments, the arm spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod in a second direction opposite the first direction translates the spinner distally to the handle. In some embodiments, rotating the handle in a first direction tightens the lock against the primary button.

Another aspect provided herein is a suture-button system comprising: one or more a suture strands; a primary button having a plurality of primary apertures, and a primary threaded portion; a secondary button having a plurality of secondary apertures; and a lock having a secondary threaded portion, wherein the secondary threaded portion is removably coupled to the primary threaded portion; wherein each primary aperture has one or more of the plurality of sutures strands inserted therethrough, wherein each secondary aperture has one or more of the plurality of sutures strands inserted therethrough, and wherein coupling the secondary threaded portion of the lock to the threaded portion prevents each of the plurality of suture strands from translating through one or more of the plurality of first button apertures. In some embodiments, the plurality of primary apertures comprises 2, 3, 4, or 5 primary apertures. In some embodiments, the plurality of primary apertures are equally spaced on the primary button. In some embodiments, the plurality of primary apertures are equally spaced on the primary button in a circular array. In some embodiments, the plurality of primary apertures are equally spaced on the primary button in a circular array about the primary threaded portion. In some embodiments, the plurality of primary apertures are equally spaced on the primary button in a circular array about a center axis of the secondary button. In some embodiments, a proximal surface of the primary button comprises a countersink. In some embodiments, the primary threaded portion comprises a female threaded portion. In some embodiments, the secondary threaded portion comprises a male threaded portion. In some embodiments, the primary threaded portion comprises a male threaded portion. In some embodiments, the secondary threaded portion comprises a female threaded portion. In some embodiments, the plurality of secondary apertures comprises 2, 3, 4, or 5 secondary apertures. In some embodiments, a distal surface of the secondary button comprises a channel connecting two or more of the plurality of secondary apertures. In some embodiments, one or more edges of the secondary button are rounded or chamfered. In some embodiments, an aspect ratio between the length and width of the secondary button is about 1:1 so about 4:1. In some embodiments, the lock comprises a head and wherein the secondary threaded portion extends from the head. In some embodiments, a distal surface of the head is tapered outwards from a center axis of the lock. In some embodiments, the distal surface of the head is tapered outwards from a center of the lock by about 20° to about 89°. In some embodiments, the lock comprises a driver feature, an alignment feature, or both. In some embodiments, the driver feature is opposite the secondary threaded portion. In some embodiments, the driver feature and the alignment feature are generally concentric. In some embodiments, the driver feature is proximal to the alignment feature. In some embodiments, a maximum inner diameter of the driver feature is greater than a maximum inner diameter of the alignment feature. In some embodiments, the driver feature comprises a Philips driver feature, a flathead driver feature, a torx driver feature, a hex driver feature, or a square socket feature. In some embodiments, the alignment feature has a cross sectional shape comprising a circle, a triangle, a square, a pentagon, a hexagon, an octagon, or any combination thereof. In some embodiments, they system further comprises a lock driver comprising a driving feature that is configured to rotate the lock about the primary button. In some embodiments, the lock driver further comprises an aligning feature configured to align the lock driver to the alignment feature of the lock. In some embodiments, the alignment feature is distal to the driving feature. In some embodiments, at least a portion of the lock extends beyond a distal face of the primary button when the primary button is coupled to the lock. In some embodiments, a distal face of the primary button extends beyond a distal face of the lock when the primary button is coupled to the lock. In some embodiments: the plurality of primary apertures comprises two primary apertures; the plurality of secondary apertures comprises two secondary apertures; the one or more suture strands consists of one suture strand; and the one suture strand is inserted through a first primary aperture, through a first secondary aperture, through a second secondary aperture, and through a second primary aperture. In some embodiments: the plurality of primary apertures comprises four primary apertures; the plurality of secondary apertures comprises two secondary apertures; the one or more a suture strands consists of two suture strands; a first suture strand is inserted through a first primary aperture, through a first secondary aperture, through a second secondary aperture, and through a second primary aperture; and a second suture strand is inserted through a third primary aperture, through the first secondary aperture, through the second secondary aperture, and through a fourth primary aperture; In some embodiments: the plurality of primary apertures comprises four primary apertures; the plurality of secondary apertures comprises two secondary apertures; the one or more a suture strands consists of two suture strands; a first suture strand is inserted through a first primary aperture, through a first secondary aperture, through a second secondary aperture, and through a second primary aperture; and a second suture strand is inserted through a third primary aperture, through the second secondary aperture, through the first secondary aperture, and through a fourth primary aperture; In some embodiments, the first primary aperture and the second primary aperture are adjacent. In some embodiments, the first primary aperture and the second primary aperture are nonadjacent. In some embodiments, the system further comprises a tightening tool comprising: a threaded rod; a knob coupled to a proximal end of the threaded rod; a collar coupled to the threaded rod; an arm spinner between the knob and the tensioning collar, wherein the arm spinner comprises an aperture accepting the threaded rod; and a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driving feature of the lock. In some embodiments, the arm spinner further comprises a terminator channel accepting the terminator. In some embodiments, the arm spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature. In some embodiments, the arm spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod in a second direction opposite the first direction translates the spinner distally towards the handle. In some embodiments, rotating the handle in a first direction tightens the lock against the primary button. In some embodiments, the suture is a #1 size suture, a #2 size suture, a #3 size suture, a #4 size suture, a #5 size suture, a #6 size suture, or a #7 size suture. In some embodiments, the suture has a length of about 100 mm to about 1,200 mm. In some embodiments, the system comprise 2, 3, 4, 5, 6 or more suture strands. In some embodiments, the system comprise a first suture strand and a second suture strand, wherein at least a portion of the first suture strand passes within at least a portion of the second suture strand to form a suture bundle 170. In some embodiments, the portion of the first suture strand that passes within the second suture strand is a mesial portion of the first suture. In some embodiments, the portion of the second suture strand through which the first suture strand passes is a mesial portion of the second suture.

Another aspect provided herein is a suture-button assembly comprising: two or more suture-button systems; and an insertion plate comprising a plurality of insertion plate apertures, each insertion plate aperture accepting at least one suture strand. In some embodiments, the plurality of insertion plate apertures comprises 2, 3, 4, 5, 6, or more insertion plate apertures. In some embodiments, the assembly further comprises an insertion screw, wherein the insertion plate further comprises a screw hole; configured to removable couple to the insertion screw. In some embodiments, the screw hole is positioned between two of the plurality of insertion plate apertures. In some embodiments, the insertion screw comprises a first portion configured to removably couple to the screw hole and a second portion configured to attach to a bone of a patient.

Another aspect provided herein is a method of assembling a suture button, the method comprising: providing the suture-button system of any one or more embodiments described herein, wherein: the plurality of primary apertures comprises a first primary aperture and a second primary aperture; the plurality of secondary apertures comprises a first secondary aperture and a second secondary aperture; and the one or more a suture strands consists of one suture strand; inserting the one suture strand through the first primary aperture; inserting the one suture strand through the first secondary aperture; inserting the one suture strand through the second secondary aperture; and inserting the one suture strand through the second primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the suture strand from translating through the first primary aperture and the second primary aperture. In some embodiments, the method further comprises providing the tightening tool of any one or more embodiments described herein. In some embodiments, the secondary threaded portion and the primary threaded portion are coupled by the tightening tool. In some embodiments, the method further comprises tightening the suture strand with respect to the primary button, the secondary button, or both, with the tightening tool.

Another aspect provided herein is a method of assembling a suture button, the method comprising: providing the suture-button system of any one or more embodiments described herein, wherein: the plurality of primary apertures comprises a first primary aperture, a second primary aperture, a third primary aperture, and a fourth primary aperture; the plurality of secondary apertures comprises a first secondary aperture and a second secondary aperture; and the one or more a suture strands consists of a first suture strand and a second suture strand; inserting the first suture strand through the first primary aperture; inserting the first suture strand through the first secondary aperture; inserting the first suture strand through the second secondary aperture; inserting the first suture strand through the second primary aperture; inserting the second suture strand through the third primary aperture; inserting the second suture strand through the first secondary aperture; inserting the second suture strand through the second secondary aperture; and inserting the second suture strand through the fourth primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the first suture strand and the second suture strand from translating through the plurality of primary apertures. In some embodiments, the method further comprises providing the tightening tool of any one or more embodiments described herein. In some embodiments, the secondary threaded portion and the primary threaded portion are coupled by the tightening tool. In some embodiments, the method further comprises tightening the first suture strand and the second suture strand with respect to the primary button, the secondary button, or both, with the tightening tool.

Another aspect provided herein is a method of assembling a suture button, the method comprising: providing the suture-button system of any one or more embodiments described herein, wherein: the plurality of primary apertures comprises a first primary aperture, a second primary aperture, a third primary aperture, and a fourth primary aperture; the plurality of secondary apertures comprises a first secondary aperture and a second secondary aperture; and the one or more a suture strands consists of a first suture strand and a second suture strand; inserting the first suture strand through the first primary aperture; inserting the first suture strand through the first secondary aperture; inserting the first suture strand through the second secondary aperture; inserting the first suture strand through the second primary aperture; inserting the second suture strand through the third primary aperture; inserting the second suture strand through the second secondary aperture; inserting the second suture strand through the first secondary aperture; and inserting the second suture strand through the fourth primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the first suture strand and the second suture strand from translating through the plurality of primary apertures. In some embodiments, the method further comprises providing the tightening tool of any one or more embodiments described herein. In some embodiments, the secondary threaded portion and the primary threaded portion are coupled by the tightening tool. In some embodiments, the method further comprises tightening the first suture strand and the second suture strand with respect to the primary button, the secondary button, or both, with the tightening tool.

EXAMPLES

The following illustrative examples are representative of embodiments of the systems, and methods described herein and are not meant to be limiting in any way.

Example 1—Syndesmosis Repair

In one example of an ankle syndesmosis repair, suture-button assembly is used, wherein the secondary button rests on the tibia and the primary button rests on the fibula. The plate of the suture-button assembly is placed on the fibula across a fracture, so that one suture-button system is deployed on either side of the fracture. The insertion screw is used to temporarily fixate the plate to the fibula while the suture-button system is deployed.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A suture-button system comprising:

(a) a plurality of suture strands;

(b) a primary button having a plurality of primary apertures, wherein:

(i) a first suture strand of the plurality of suture strands is inserted through a first set of primary apertures of the plurality of primary apertures;

(ii) a second suture strand of the plurality of suture strands is inserted through a second set of primary apertures of the plurality of primary apertures;

(iii) the plurality of primary apertures comprises at least eight primary apertures;

(iv) the first set of primary apertures is different from the second set of primary apertures;

(v) the first set of primary apertures are equally spaced relative to each other in a least a partially circular array; and (vi) one or both of the first suture strand and the second suture strand is inserted through the respective first set of primary apertures and second set of primary apertures in a weaving configuration; and (c) a secondary button having a plurality of secondary apertures, wherein:

(i) the first suture strand and the second suture strand are each inserted through a first and second secondary aperture of the plurality of secondary apertures, wherein the suture-button system is configured to clamp at least one targeted tissue of a subject between a distal surface of the primary button and a proximal surface of the secondary button upon application of a tension to one or both of the first suture strand and the second suture strand.

2. The suture-button system of claim 1, wherein the first set of primary apertures and the second set of primary apertures are disposed symmetrical to each other on the primary button.

3. The suture-button system of claim 1, wherein the primary button comprises a primary threaded portion for receiving a secondary threaded portion of a lock, so as to removably couple the lock to the primary button, such that one or both of the first suture strand and the second suture strand are prevented from translating through the respective primary apertures and thereby securing the clamping of the targeted tissue.

4. The suture-button system of claim 3, wherein the primary threaded portion comprises a female threaded portion.

5. The suture-button system of claim 3, wherein the lock comprises a head and wherein the secondary threaded portion extends from the head.

6. The suture-button system of claim 5, wherein a distal surface of the head is tapered outwards from a center axis of the lock.

7. The suture-button system of claim 3, wherein the lock comprises a driver feature, an alignment feature, or both.

8. The suture-button system of claim 7, wherein the driver feature and the alignment feature are generally concentric.

9. The suture-button system of claim 1, wherein a distal surface of the secondary button comprises a channel connecting two or more of the plurality of secondary apertures.

* * * * *